(12) United States Patent
Kawabata et al.

(10) Patent No.: US 6,891,028 B1
(45) Date of Patent: May 10, 2005

(54) NUCLEIC ACIDS ENCODING TRANSFERRIN RECEPTOR-LIKE PROTEINS

(75) Inventors: Hiroshi Kawabata, Los Angeles, CA (US); H. Phillip Koeffler, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 09/358,755

(22) Filed: Jul. 22, 1999

Related U.S. Application Data

(60) Provisional application No. 60/107,502, filed on Nov. 6, 1998.

(51) Int. Cl.[7] .................. C07H 21/04; C12N 15/00; C12N 15/12; C12N 15/63
(52) U.S. Cl. .................. 536/23.5; 435/69.1; 435/320.1; 435/325
(58) Field of Search .................. 435/320.1, 69.1, 435/325; 536/23.5

(56) References Cited

PUBLICATIONS

Hillier, LD et al. Generation and analysis of 280,000 human expressed sequence tags. Genome Research, vol. 6:807–828, 1996.*
Chonn A. et al. Recent advanecs in liposomal drug–delivery systems. Current opinion in Biotechnology 1995 6:698–708.*
Mikayama T. Molecular cloning and functional expression of a cDNA encoding glycosylation–inhibiting factor. Proc. Natl. Acad. Sci. USA vol. 90, pp. 10056–10060, 1993.*
Voet et al. Biochemistry. 1990. John Wiley & Sons, Inc.. pp. 126–128 and 228–234.*
Stratagene Catalogue, p. 66, 1991.*
& DATABASE EMBL 'Online! Accession No. AF053356, Jun. 13, 1998 "*Homo sapiens* chromosome 7q22 sequence, complete sequence" the whole document.
& DATABASE EMBL 'Online! Accession No. 005422, Nov. 1, 1998 "Transferrin–Receptor2" the whole document.
& DATABASE EMBL 'Online! Accession No. AF085928, Sep. 3, 1998 "*Homo sapiens* full length insert cDNA clone YR5OHO4" XP002135481 CC transferrin–receptor2.
& DATABASE EMBL 'Online! Accession No. X01060 Nov. 7, 1985 "Human mRNA for transferrin receptor" the whole document.
Glockner, G. et al.: "Large–scale sequencing of two regions in human chromosome 7q22: Analysis of..." GENOME Res, vol. 8, Oct. 1998, pp. 1060–1073 table 3, p. 1067, paragraph 1.
Schneider, C. et al.: "Primary structure of human transferrin receptor deduced from the mRNA sequence" NATURE, vol. 311, 1984, pp. 675–678.
Brooks, D. et al.: "Phase Ia trial of murine immunoglobulin A antitransferrin receptor antitransferrin receptor antibody 42/6" Clin. Cancer Res., vol. 1, No. 11, Nov. 1995 pp. 1259–1265.
Nikinmaa, B. et al.: "Monoclonal antibodies to a purified human transferrin receptor" Scand. J. Immunol., vol. 20, No. 5, Nov. 1984 pp. 441–447.
Trinder, D. et al.: "Transferrin Receptor—Independent Uptake of Differic Transferrin by Human Hepatoma Cells with Antisense Inhibition of Receptor Expression" Hepatology, vol. 23, No. 6, Jun. 1996, pp. 1512–1520.

* cited by examiner

*Primary Examiner*—Elizabeth Kemmerer
*Assistant Examiner*—Joseph F. Murphy
(74) *Attorney, Agent, or Firm*—Pillsbury Winthrop LLP

(57) ABSTRACT

The present invention provides isolated nucleic acids encoding TfR2 polypeptides, or fragments thereof, and isolated TfR2 polypeptides encoded thereby. Further provided are vectors containing the nucleic acids of the present invention, host cells transformed therewith, antisense oligonucleotides thereto and compositions containing antibodies that specifically bind to invention polypeptides. Methods of detecting TfR2 protein in a cell are also provided.

19 Claims, 10 Drawing Sheets

FIG. 2

Exon 3 of TfR2-α

CCTTCCTACTGGGCTACGTCGCCTTCCGAGGGTCCTGCCAGGCGTGCGGAGACTCTGTGT

TGGTGGTCAGTGAGGATGTCAACTATGAGCCTGACCTGGATTTCCACCAGGGCAGACTCT
      Primer-D
ACTGGAGCGACCTCCAGGCCATGTTCCTGCAGTTCCTGGGGGAGGGGCGCCTGGAGGACA

CCATCAG

Exon 4 (boxed sequence is in the TfR2-β only)

GCGTCCGCGGGGAGCGCTCTTTTCCTAAACTCAGGAACCCCTCGCCGCCCCTGCCCCTGG

CGACCCCACGTCTCTGGCATCCTTCCCTCTTCCCTCCCTCTCCTCCGGGCGCCCAAAAAA
      Primer-C
GTCCCCACCTCTCCCCGCTTAGGCAAACCAGCCTTCGGGAACGGGTGGCAGGCTCGGCCG GGATGGCCGCTCTGACTCAGGACATTCGCGCGGCGCTCTCCCGCCAGAAGCTGGACCACG
                                                               Primer-A
TGTGGACCGACACGCACTACGTGGGGCTGCAATTCCCGGATCC Exon 5 (common for both α- and β-forms)

GGCTCACCCCAACACCCTGCACTGGGTCGATGAGGCCGGGAAGGTCGGAGAGCAGCTGCC
                    Primer-E
GCTGGAGGACCCTGACGTCTACTGCCCCTACAGCGCCATCGGCAACGTCACG

FIG. 3

```
TfR2-α    1    M E R L W G L F Q R A Q Q L S P R S S Q T V Y Q R V E G P R K G H L E E E E E D G E E G A E T L A H
TfR       1    M - - - M D Q A R S A F S N L F G G E P L S Y T R F S L A R - - - - - - - - - - - - Q V D G D N S
PSMA      1    M - - - - - - - - - - - - - - - - - - - - - - - - - - - - - - - - - - - - - - - - - - - - - - -

TfR2-α   51    F C P M E L R G P E P L G S R P R Q P N L I P W A A A G R R A A P Y L V L T A L L I F T G A F L L G
TfR      35    H V E M K L A V D E E E N A D N N T K A N V T K P K R C S G S I C Y G T I A V I V F F L I G F M I G
PSMA      2    - - - - - - - - - - - - - W N L L H E T D S A V A T A R R P R W L C A G A L V L A G G F F L L G

TfR2-α  101    Y V A F - R G S C - Q A C G D S V L V V S E D V N Y E P D L D F H Q G R - L Y W S D L Q A M F L Q F
TfR      85    Y L G Y C K G V E P K T E C E R L A G T E S P V R E E P G E D F P A A R R L Y W D D L K R K L S E K
PSMA     37    F L F - - - G W F I K S S N E A T N I I T P K H N M K A - - - - - - - - - - - - - - - - - - - F

TfR2-α  148    L G E G R L E D T I R - - - Q T S L R E R V A G S A G M A A L T Q D I R A A L S R Q K L D H V W T D
TfR     135    L D S T D F T S T I K L L N E N S Y V P R E A G S Q K D E N L A L Y V E N Q F R E F K L S K V W R D
PSMA     62    L D E L K A E N I K K F L Y N F T Q I P H L A G T E Q N F Q L A K Q I Q S Q W K E F G L D S V E L A

TfR2-α  195    T H Y V G L Q F - P D P A H P N T L H W V D E A G K V G E Q - - L P L E D P D V Y C P Y S A I G N V
TfR     185    Q H F V K I Q V - K D S A - Q N S V I I V D K N G R L V Y - - - L V E N P L G G Y V A Y S K A A T V
PSMA    112    - H Y D V L L S Y P N K T H P N Y I S I I N E D G N E I F N T S L F E P P P P G Y E N V S D I V P P

TfR2-α  242    T - - - - - - - - - - G E L V Y A H Y G R P E D L Q D L R A R G V D P V - G R L L L V R V G V I S F
TfR     229    T - - - - - - - - - - G K L V H A N F G T K K D F E D L - - - - Y T P V N G S I V I V R A G K I T F
PSMA    161    F S A F S P Q G M P E G D L V Y V N Y A R T E D F F K L E R D M K I N C S G K I V I A R Y G K V F R

TfR2-α  281    A Q K V T N A Q D F G A Q G V L I Y P E P A D - F S Q D P P K P S L S S Q Q A V Y G H V H - - - - -
TfR     265    A E K V A N A E S L N A I G V L I Y M D Q T K - F - P I V N A E - - - - L S F F G H A H - - - - -
PSMA    211    G N K V K N A Q L A G A K G V I L Y S D P A D Y F A P G V K S Y P D G W N L P G G G V Q R G N I L N

TfR2-α  325    L - G T G D P Y T P G F P S F N Q T Q F P P V A - S S G L P S I P A Q P I S A D I A S R L L R K L K
TfR     303    L - G T G D P Y T P G F P S F N H T Q F P P S R - S S G L P N I P V Q T I S R A A A E K L F G N M E
PSMA    261    L N G A G D P L T P G Y P A N E Y A Y R R G I A E A V G L P S I P V H P I G Y Y D A Q K L L E K M G

TfR2-α  373    G P V A P Q E - - W Q G S L L G S P Y H L G P G P R - - - - - - - L R L V V N N H R T S T P I N N
TfR     351    G D - C P S D - - W K - - - - - - - - - T D S T C R M V T S E S K N V K L T V S N V L K E I K I L N
PSMA    311    G S - A P P D S S W R G S L K - V P Y N V G P G F T G N F S T Q K - V K M H I H S T N E V T R I Y N

TfR2-α  413    I F G C I E G R S E P D H Y V V I G A Q R D A W G P G A A K S A V G T A I L L E L V R T F S S M V S
TfR     389    I F G V I K G F V E P D H Y V V V G A Q R D A W G P G A A K S G V G T A L L L K L A Q M F S D M V L
PSMA    358    V I G T L R G A V E P D R Y V I L G G H R D S W V F G G I D P Q S G A A V V H E I V R S F G T L K K

TfR2-α  463    N - G F R P R R S L L F L I S W D G G D F G S V G S T E W L E G Y L S V L H L K A V V Y V S L D N A V
TfR     439    K D G F Q P S R S I I F A S W S A G D F G S V G A T E W L E G Y L S S L H L K A F T Y I N L D K A V
PSMA    408    E - G W R P R R T I L F A S W D A E E F G L L G S T E W A E E N S R L L Q E R G V A Y I N A D S S I

TfR2-α  512    L G D D K F H A K T S P L L T S L I E S V L K Q V D S P N H - - S G Q T L Y E Q V V F T N P S W D A
TfR     489    L G T S N F K V S A S P L L Y T L I E K T M Q N V K H P V - - - T G Q F L Y Q D S N W A S K V - E K
PSMA    457    E G N Y T L R V D C T P L M Y S L V H N L T K E L K S P D E G F E G K S L Y E S W T K K S P S P E F

TfR2-α  560    E V I R P L P M D S S A Y S F T A F V - - - G V P - - - A V E F S F M E D D Q A Y P F L H T K E D T
TfR     535    L T L D N A A F P F L A Y S - - - - - - - G I P - - - A V S F C F C E D T D - Y P Y L G T T M D T
PSMA    507    S G M P R I S K L G S G N D F E V F F Q R L G I A S G R A R Y T K N W E T N K F S G Y P L Y H S V Y

TfR2-α  604    Y E N L H K V L Q G R L P A V A Q A - - V A Q L A G Q L L I R L S H D R L L P L D F G R Y G D V V L
TfR     573    Y K E L - I E R I P E L N K V A R A - - A A E V A G Q F V I K L T H D V E L N L D Y E R Y N S Q L L
PSMA    557    E T Y E - L V E K F Y D P M F K Y H L T V A Q V R G G M V F E L A N S I V L P F D C R D Y A V V L R

TfR2-α  652    R H I G N L N E F S G D L K - A R G L T L Q W V Y S A R G D Y I R A A E K L R Q E I Y S S E E R D E
TfR     620    S F V R D L N Q Y R A D I K - E M G L S L Q W L Y S A R G D F F R A T S R L T T D F G N - A E K T D
PSMA    606    K Y A D K I Y S I S M K H P Q E M K T Y S V S F D S L F S A V K N F T E I A S K F S E R L Q D F D K

TfR2-α  701    R L T R M Y - - - N V R I M R V E F Y F L S Q Y V S P A D S P F - R H I F M G R G D H T L G A L L D
TfR     668    R F V - M K K L - N D R V M R V E Y H F L S P Y V S P K E S P F - R H V F W G S G S H T L P A L L E
PSMA    656    S N P I V L R M M N D Q L M F L E R A F I D P L G L P D R - P F Y R H V I Y A P S S H N K Y A G E S

TfR2-α  747    H L R L L R S N S S G T P G A T S S T G F Q E S R F R R Q L A L L T W T L Q G A A N A L S G D V W N
TfR     715    N L K L R K Q N N - - - - - - - - G A F N E T L F R N Q L A L A T W T I Q G A A N A L S G D V W D
PSMA    705    F P G I Y D A L F D I E S K V D P S K A W G E V K - R Q I Y V A A F T V Q A A A E T L S - E V A D

TfR2-α  797    I D N N F
TfR     756    I D N E F
PSMA    752    I
```

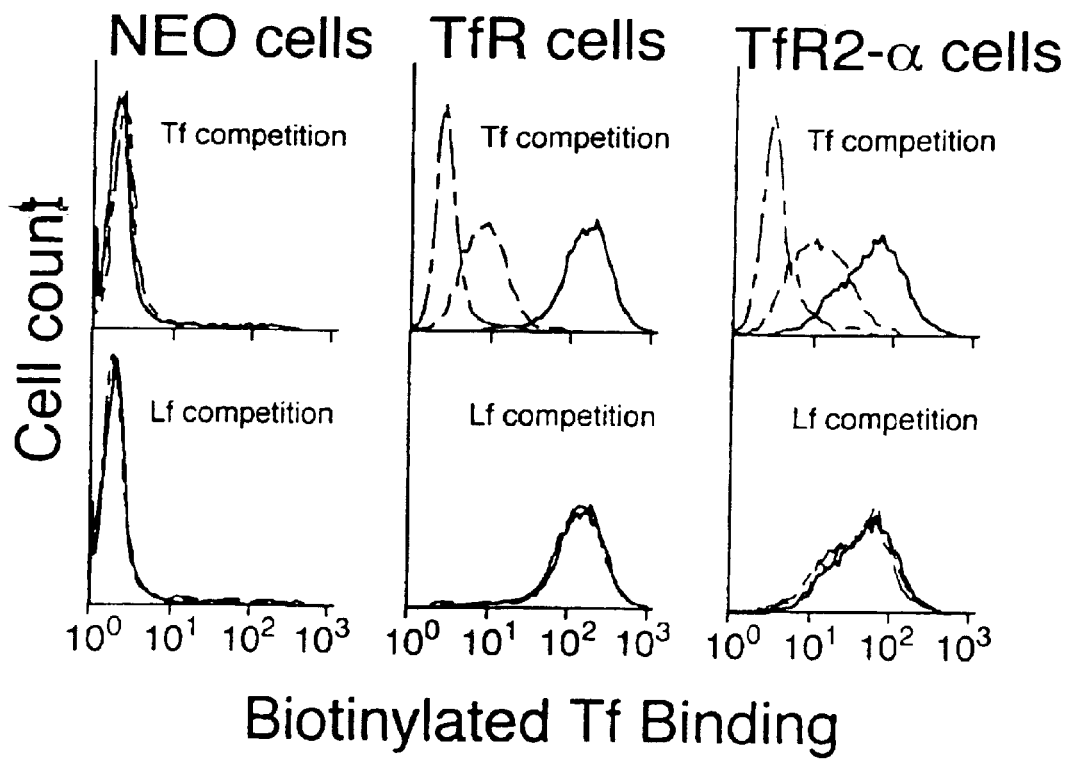
FIG. 6B
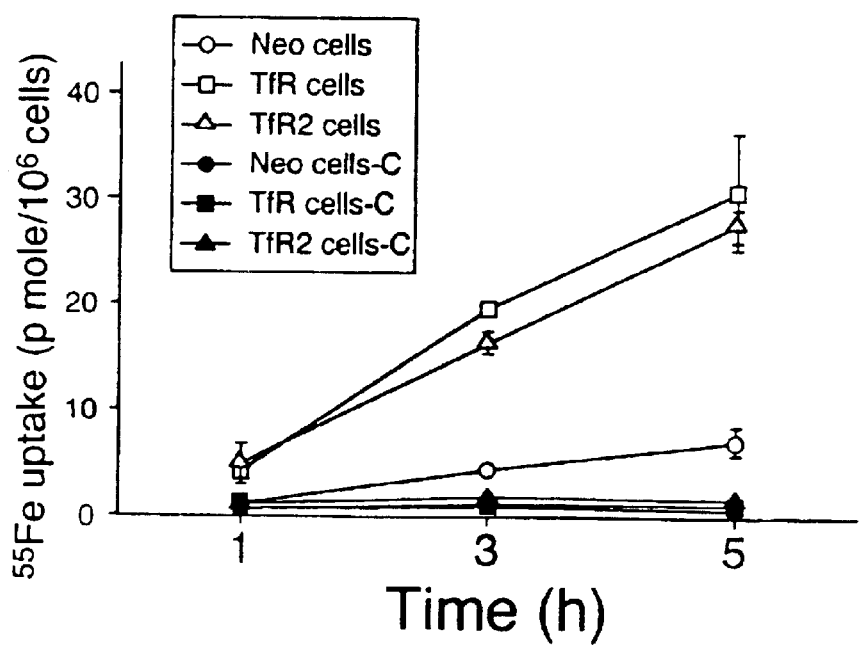

Fig. 7 alpha amino acid sequence

MERLWGLFQRAQQLSPRSSQTVYQRVEGPRKGHLEEEEEDGEEGAETLAHFCPMELRGPEPLGSRPRQPNLIPWAAAGRR
AAPYLVLTALLIFTGAFLLGYVAFRGSCQACGDSVLVVSEDVNYEPDLDFHQGRLYWSDLQAMFLQFLGEGRLEDTIRQT
SLRERVAGSAGMAALTQDIRAALSRQKLDHVWTDTHYVGLQFPDPAHPNTLHWVDEAGKVGEQLPLEDPDVYCPYSAIGN
VTGELVYAHYGRPEDLQDLRARGVDPVGRLLLVRVGVISFAQKVTNAQDFGAQGVLIYPEPADFSQDPPKPSLSSQQAVY
GHVHLGTGDPYTPGFPSFNQTQFPPVASSGLPSIPAQPISADIASRLLRKLKGPVAPQEWQGSLLGSPYHLGPGPRLRLV
VNNHRTSTPINNIFGCIEGRSEPDHYVVIGAQRDAWGPGAAKSAVGTAILLELVRTFSSMVSNGFRPRRSLLFISWDGGD
FGSVGSTEWLEGYLSVLHLKAVVYVSLDNAVLGDDKFHAKTSPLLTSLIESVLKQVDSPNHSGQTLYEQVVFTNPSWDAE
VIRPLPMDSSAYSFTAFVGVPAVEFSFMEDDQAYPFLHTKEDTYENLHKVLQGRLPAVAQAVAQLAGQLLIRLSHDRLLP
LDFGRYGDVVLRHIGNLNEFSGDLKARGLTLQWVYSARGDYIRAAEKLRQEIYSSEERDERLTRMYNVRIMRVEFYFLSQ
YVSPADSPFRHIFMGRGDHTLGALLDHLRLLRSNSSGTPGATSSTGFQESRFRRQLALLTWTLQGAANALSGDVWNIDNN
F

Fig. 8 alpha DNA sequence

```
CTGCAGGCTTCAGGAGGGGACACAAGCATGGAGCGGCTTTGGGGTCTATTCCAGAGAGcGCAACAACTGTCCCCAAGATC
CTCTCAGACCGTCTACCAGCGTGTGGAAGGCCCCCGGAAAGGGCACCTGGAGGAGGAAGAGGAAGACGGGGAGGAGGGGG
CGGAGACATTGGCCCACTTCTGCCCCATGGAGCTGAGGGGCCCTGAGCCCCTGGGCTCTAGACCCAGGCAGCCAAACCTC
ATTCCCTGCGCGGCAGCAGGACGGAGGGCTGCCCCCTACCTGGTCCTGACGGCCCTGCTGATCTTCACTGGGGCTTCCT
ACTGGCTACGTCGCCTTCCGAGGGTCCTGCCAGGCGTGCGGAGACTCTGTGTTGGTGGTCAGTGAGGATGTCAACTATG
AGCCTGACCTGGATTTCCACCAGGGcagactctactggaGcgacCtccaGgccatgttcctgcagttcctggggqaGgqg
cgcctggaGgaCaccaTCAGGCAAACCAGCCTTCGGGAACGGGTGGCAGGCTCGGCCGGGATGGCCGCTCTGACTCAGGA
CATTCGCGCGGCGCTCTCCCGCCAGAAGCTGGACCACGTGTGGACCGACACGCACTACGTGGGGCTGCAATTCCCGGATC
CGGCTCACCCCAACACCCTGCACTGGGTCGATGAGGCCGGGAAGGTCGGAGAGCAGCTGCCGCTGGAGGACCCTGACGTC
TACTGCCCCTACAGCGCCATCGGCAACGTCACGGGAGAGCTGGTGTAcGCCCACTACGGGCGGCCCGAAGACCTGCAGGA
CcTGCGGGCCAGGGGCGTGGATCCACTGGGCCGCCTGCTGCTGGTGCGCGTGGGGGTGATCagcTTCGCCCAGAAGGTGA
CCAATGCTCAGGACTTCGGGGCTCAAGGAGTGCTCATATACCCAGAGCCAGCGGACTTCTCCCAGGACCCACCCAAGCCA
AGCCTGTCCAGCCAGCAGGCAGTGTATGGACATGTGCACCTGGGAACTGGAgACCCcTACACACCTGGCTTCCCTTCCTT
CAATCAAACCCAGTTCCCTCCAGTTGCATCATCAGGCCTTCCCAGCATCCcAGCCCAGCCCATCAGTGCAGACATTGCCT
CCCGCCTGCTGAGGAAGCTCAAAGGCCCTGTGGCCCCCAAGAATGGCAGGGGAGCCTGCTAGGCTCCCCTTATCACCTG
GGCCCCGGGCCACGACTGCGGCTAGTGGTCAACAATCACAGGACCTCCACCCCCATCAACAACATCTTCGGCTGCATCGA
AGGCCGCTCAGAGCCAGATCACTACGTTGTCATCGGGGCCAGAGGGATGCATGGGGCCCAGGAGCAGCTAAATCCGCTG
TGGGACGGCTATACTCCTGGAGCTGGTGCGGACCTTTTCCTCCATGGTGAGCAACGGCTTCCGGCCCCGCAGAAGTCTC
CTCTTCATCAGCTGGGACGGTGGTGACTTTGGAAGCGTGGGCTCCACGGAGTGGCTAGAAGGCTACCTCAGCGTGCTGCA
CCTCAAAGCCGTAGTGTACGTGAGCCTGGACAACGCAGTGCTGGGGGATGACAAGTTTCATGCCAAGACCAGCCCCCTTC
TGACAAGTCTCATTGAGAGTGTCCTGAAGCAGGTGGATTCTCCCAACCACAGTGGGCAGACTCTCTATGAACAGGTGGTG
TTCACCAATCCCAGCTGGGATGCTGAGGTGATCCGGCCCCTACCCATGGACAGCAGTGCCTATTCCTTCACGGCCTTTGT
GGGAGTCCCTGCCGTCGAGTTCTCCTTTATGGAGGACGACCAGGCCTACCCATTCCTGCACACAAAGGAGGACACTTATG
AGAACCTGCATAAGGTGCTGCAAGGCCGCCTGCCGCCGTGGCCCAGGCCGTGGCCCAGCTCGCAGGGCAGCTCCTCATC
CGGCTCAGCCACGATCGCCTGCTGCCCCTCGACTTCGGCCGCTACGGGACGTCGTCCTCAGGCACATCGGGAACCTCAA
CGAGTTCTCTGGGGACCTCAAGGCCCGCGGGCTGACCCTGCAGTGGGTGTACTCGGCGCGGGGGGACTACATCCGGGCGG
CGGAAAAGCTGCGGCAGGAGATCTACAGCTCGGAGGAGAGAGACGAGCGACTGACACGCATGTACAACGTGCGCATAATG
CGGGTGGAGTTCTACTTCCTTTCCCAGTACGTGTCGCCAGCCGACTCCCCGTTCCGCCACATCTTCATGGGCCGTGGAGA
CCACACGCTGGGCGCCCTGCTGGACCACCTGCGGCTGCTGCGCTCCAACAGCTCCGGGACCCCCGGGGCCACCTCCTCCA
CTGGCTTCCAGGAGAGCCGTTTCCGGCGTCAGCTAGCCCTGCTCACCTGGACGCTGCAAGGGGCAGCCAATGCGCTTAGC
GGGGATGTCTGGAACATTGATAACAACTTCTGAGGCCCTGGGGATCCTCACATCCCCGTCCCCCAGTCAAGAGCTCCTCT
GCTCCTCGCTTGAATGATTCAGGGTCAGGGAGGTGGCTCAGAGTCCACCTCTCATTGCTGATCAATTTCTCATTACCCCT
ACACATCTCTCCACGGAGCCCAGACCCCAGCACAGATATCCACACACCCCAGCCCTGCAGTGTAGCTGACCCTAATGTGA
CGGTCATACTGTCGGTTAATCAGAGAGTAGCATCCCTTCAATCACAGCCCCTTCCCCTTTCTGGGGTCCTCCATACCTAG
AGACCACTCTGGGAGGTTTGCTAGGCCCTGGGACCTGGCCAGCTCTGTTAGTGGGAGAGATCGCTGGCACCATAGCCTTA
TGCCCAACAGGTGGTCTGTGGTGAAAGGGGCGTGGAGTTTCAATATCAATAAACCACCTGATATCAATAAGCCAAAA
```

Fig. 3 beta DNA sequence

```
GCGTCCGCGGGAGCGCTCTTTTCCTAAACTCAGGAACCCCTCGCCGCCCCTGCCCTGGCGACCCCACGTCTCTGGCAT
CCTTCCCTCTTCCCTCCCTCTCCTCCGGGCGCCCAAAAAAGTCCCCACCTCTCCCCGCTTAGGCAAACCAGCCTTCGGGA
ACGGTGGCAGGCTCGGCCGGGATGGCCGCTCTGACTCAGGACATTCGCGCGGCGCTCTCCCGCCAGAAGCTGGACCACG
TGTGGACCGACACGCACTACGTGGGGCTGCAATTCCCGGATCCGGCTCACCCCAACACCCTGCACTGGGTCGATGAGGCC
GGGAAGGTCGGAGAGCAGCTGCCGCTGGAGGACCCTGACGTCTACTGCCCCTACAGCGCCATCGGCAACGTCACGGGAGA
GCTGGTGTAGGCCCACTACGGGCGGCCCGAAGACCTGCAGGACCTGCGGGCCAGGGGCGTGGATCCAGTGGGCCGCCTGC
TGCTGGTGCTCGTGGGTGTGATCAgCTTCGCCCAGAAGGTGACCAATGCTCAGGACTTCGGGGCTCAAGGAGTGCTCATA
TACCCAGAGCCAGCGGACTTCTCCCAGGACCCACCCAAGCCAAGCCTGTCCAGCCAGCAGGCAGTGTATGGACATGTGCA
CCTGGGAACTGGAgACCCCTACACACCTGGCTTCCCTTCCTTCAATCAAACCCAGTTCCCTCCAGTTGCATCATCAGGCC
TTCCCAGCATCCCAGCCCAGCCCATCAGTGCAGACATTGCCTCCCGCCTGCTGAGGAAGCTCAAAGGCCCTGTGGCCCCC
CAAGAATGGCAGGGGAGCCTCCTAGGCTCCCCTTATCACCTGGGCCCCGGGCCACGACTGCGGCTAGTGGTCAACAATCA
CAGGACCTCCACCCCATCAACAACATCTTCGGCTGCATCGAAGGCCGCTCAGAGCCAGATCACTACGTTGTCATCGGGG
CCCAGAGGGATGCATGGGGCCCAGGAGCAGCTAAATCCGCTGTGGGACGGCTATACTCCTGGAGCTGGTGCGGACCTTT
TCCTCCATGGTGAGCAACGGCTTCCGGCCCCGCAGAAGTCTCCTCTTCATCAGCTGGGACGGTGGTGACTTTGGAAGCGT
GGGCTCCACGGAGTGGCTAGAAGGCTACCTCAGCGTGCTGCACCTCAAAGCCGTAGTGTACGTGAGCCTGGACAACGCAG
TGCTGGGGGATGACAAGTTTCATGCCAAGACCAGCCCCCTTCTGACAAGTCTCATTGAGAGTGTCCTGAAGCAGGTGGAT
TCTCCCAACCACAGTGGGCAGACTCTCTATGAACAGGTGGTGTTCACCAATCCCAGCTGGGATGCTGAGGTGATCCGGCC
CCTACCCATGGACAGCAGTGCCTATTCCTTCACGGCCTTTGTGGGAGTCCCTGCCGTCGAGTTCTCCTTTATGGAGGACG
ACCAGGCCTACCCATTCCTGCACACAAAGGAGGACACTTATGAGAACCTGCATAAGGTGCTGCAAGGCCGCCTGCCCGCC
GTGGCCCAGGCCGTGGCCCAGCTCGCAGGGCAGCTCCTCATCCGGCTCAGCCACGATCGCCTGCTGCCCCTCGACTTCGG
CCGCTACGGGGACGTCGTCCTCAGGCACATCGGGAACCTCAACGAGTTCTCTGGGGACCTCAAGGCCCGCGGGCTGACCC
TGCAGTGGCTGTACTCGGCGCGGGGGACTACATCCGGGCGGCGGAAAAGCTGCGGCAGGAGATCTACAGCTCGGAGGAG
AGAGACGAGCGACTGACACGCATGTACAACGTGCGCATAATGCGGGTGGAGTTCTACTTCCTTTCCCAGTACGTGTCGCC
AGCCGACTCCCCGTTCCGCCACATCTTCATGGGCCGTGGAGACCACACGCTGGGCGCCCTGCTGGACCACCTGCGGCTGC
TGCGCTCCAACAGCTCCGGGACCCCCGGGGCCACCTCCTCCACTGGCTTCCAGGAGAGCCGTTTCCGGCGTCAGCTAGCC
CTGCTCACCTGGACGCTGCAAGGGGCAGCCAATGCGCTTAGCGGGGATGTCTGGAACATTGATAACAACTTCTGAGGCCC
TGGGATCCTCACATCCCCGTCCCCCAGTCAAGAGCTCCTCTGCTCCTCGCTTGAATGATTCAGGGTCAGGGAGGTGGCT
CAGAGTCCACCTCTCATTGCTGATCAATTTCTCATTACCCCTACACATCTCTCCACGGAGCCCAGACCCCAGCACAGATA
TCCACACACCCCAGCCCTGCAGTGTAGCTGACCCTAATGTGACGGTCATACTGTCGGTTAATCAGAGAGTAGCATCCCTT
CAATCACAGCCCCTTCCCCTTTCTGGGGTCCTCCATACCTAGAGACCACTCTGGGAGGTTTGCTAGGCCCTGGGACCTGG
CCAGCTCTGTTAGTGGGAGAGATCGCTGGCACCATAGCCTTATGGCCAACAGGTGGTCTGTGGTGAAAGGGCGTGGAGT
TTCAATATCAATAAACCACCTGATATCAATAAGCCAAAA
```

NUCLEIC ACIDS ENCODING TRANSFERRIN RECEPTOR-LIKE PROTEINS

RELATED APPLICATION

This application claims the benefit of a provisional application Ser. No. 60/107,502, filed on Nov. 6, 1998 which is hereby incorporated by reference.

This invention was made with support by Grant No. CA26038-20 awarded by the National Institutes of Health.

BACKGROUND OF THE INVENTION

1. Area of the Art

The invention relates generally to the transferrin receptor family and specifically to nucleic acid encoding transferrin receptor-like proteins, and products related thereto.

2. Description of the Prior Art

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the claims. In addition, the abbreviations used are: TfR, transferrin receptor, RT-PCR, reverse transcriptase-polymerase chain reaction; Tf, transferrin; PSMA, prostate specific membrane antigen; RACE, rapid amplification of cDNA ends; G3PDH, glyceraldehyde-3-phosphate dehydrogenase; UTR, untranslated region; IRE, iron—responsive element; IRP, iron regulatory protein.

Transferrin receptor (TfR) is a key molecule involved in iron uptake by cells (1, 2). On the cell membrane the TfR homodimer binds to two diferric transferrin (Tf) molecules, resulting in internalization of the complex. In the cytoplasm, iron is released and utilized as a co-factor by several proteins, including heme, aconitase, cytochromes (3) and ribonucleotide reductase (4), or it may be stored in ferritin molecules. Since dividing cells require more iron than non-dividing cells, the expression of TfR is usually higher in rapidly dividing tissue (5), such as hematopoietic progenitor cells (6). Also, TfR expression is higher in tumor cells when compared to their normal cellular counterparts (7). The affinity of diferric Tf to TfR is modulated by HFE (8, 9).

The only other known homolog of TfR is PSMA, a human homolog of murine NAAG-peptidase (10, 11). Since the expression of PSMA is high in prostate cancer, the antibody against PSMA was approved for use as an imaging agent to detect metastasis of prostate cancer (12). The function of PSMA appears to be considerably different from that of TfR, despite the modest similarity between their extracellular domains. PSMA does not mediate endocytosis, and possesses glutamyl-carboxypeptidase activity (11, 13).

Given the importance of a transferrin receptor in an iron uptake process of cells, it is desirable to identify potential molecules which are homologous to a transferrin receptor and which perform transferrin receptor-like functions. The identification of the molecules may provide valuable tools for altering the iron uptake of specific cells. In addition, identified novel receptors may be used to identify various new ligands that have activity with other metals or other key proteins that are vital for the cells. Furthermore, since TfR expression is higher in tumor cells, the newly identified receptors may be used for diagnosing or treating tumor cells.

SUMMARY OF THE INVENTION

It is an object of the present invention to identify the potential transferrin receptor-like proteins. It is also an object of the present invention to investigate the roles of newly discovered receptors in iron metabolism in cells. It is a further object of the present invention to provide methods for diagnosing tumor cells.

Accordingly, the present invention provides isolated nucleic acids encoding novel transferrin receptor-like (TfR2) polypeptides, or fragments thereof, and isolated TfR2 polypeptides encoded thereby. Further provided are vectors containing nucleic acids of the present invention, host cells transformed therewith, antisense oligonucleotides thereto and compositions containing antibodies that specifically bind to polypeptides of the present invention. Methods of detecting TfR2 in a cell are also provided.

The invention is defined in its fullest scope in the appended claims and is described below in its preferred embodiments.

DESCRIPTION OF THE FIGURES

The above-mentioned and other features of this invention and the manner of obtaining them will become more apparent and will be best understood by reference to the following description, taken in conjunction with the accompanying drawings. These drawings depict only a typical embodiment of the invention and do not therefore limit its scope. They serve to add specificity and detail, in which:

FIG. 2 shows DNA sequences of exons 3–5 of TfR2 gene. Boxed sequences were found only in the β transcript.

FIG. 3 shows deduced amino acid sequence of TfR2-α, aligned with those for the human TfR and PSMA proteins.

FIGS. 6A, 6B and 6C show the expression and functional analysis of TfR2-α protein.

FIG. 7 is the amino acid sequence of TfR2 protein SEQ ID NO:1.

FIG. 8 is the DNA sequence of TfR2-α gene SEQ ID NO:2.

FIG. 9 is the DNA sequence of TfR2-β gene SEQ ID NO:3.

DETAILED DESCRIPTION OF THE INVENTION

Figure 1:
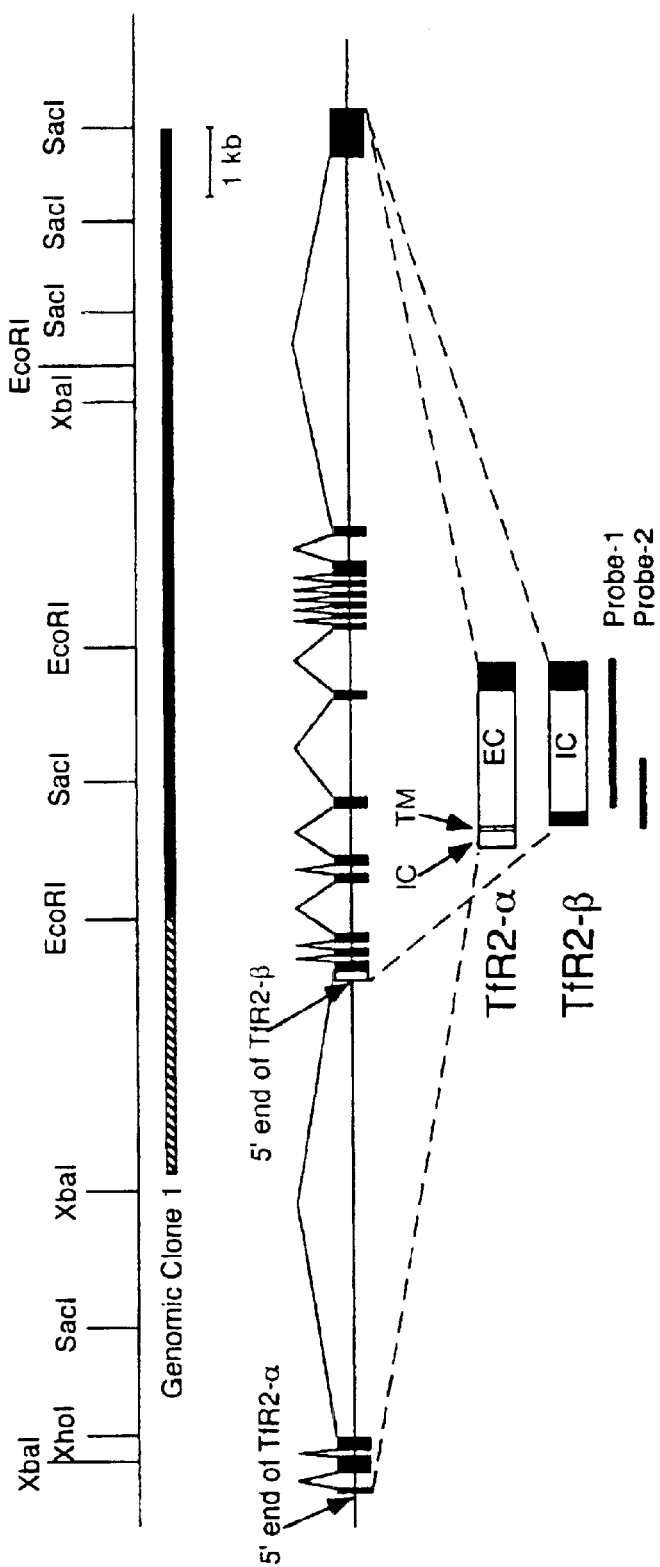
FIG. 1 is a gene map of the transferrin receptor 2 (TfR2) gene.

The present invention is based on the discovery and the cloning of a human gene homologous to transferrin receptor (TfR). For the purpose of the present invention, this gene is termed TfR2 gene. TfR2 gene is cloned, sequenced and mapped to chromosome 7q22. Two transcripts expressed from this gene are identified; they are α (about 2.9 kb) and β (about 2.5 kb) transcripts. The deduced amino acid sequences from each transcript predict the possible expression of both a membrane bound and an intracellular form of the TfR2 protein. The deduced amino acid sequence of TfR-α protein is a type II membrane protein, and shares 45% identity and 66% similarity in its extracellular domain with TfR. The TfR2-β protein lacked the amino terminal protein of the TfR2-α protein including the putative transmembrane domain. TfR deficient cells transfected with FLAG-tagged TfR2-α showed an increase of biotinylated transferrin (Tf) binding to the cell surface. In addition, these transfected cells have a marked increase of Tf-bound $^{55}$Fe uptake.

Accordingly, the present invention provides isolated nucleic acids encoding a TfR2 polypeptide. Such nucleic acids can be obtained, for example, from human chromosome 7q22. Deletion or loss of heterozygosity of this chromosomal region has been reported in several malignant diseases including myelodysplastic syndromes, acute myeloid leukemia, as well as breast, ovarian and pancreatic cancers. The nucleic acids may also be obtained from a human cDNA library such as, but not limited to, HL60 cDNA library or TF-1 cDNA library.

The term "nucleic acids" (also referred to as polynucleotides) refers to a polymer of deoxyribonucleotides or ribonucleotides, in the form of a separate fragment or as a component of a larger construction. DNA encoding the polypeptide of the invention can be assembled from cDNA fragments or from oligonucleotides which provide a synthetic gene which is capable of being expressed in a recombinant transcriptional unit. Polynucleotide sequences of the invention include DNA, RNA and cDNA sequences. In accordance with one embodiment of the present invention, nucleic acids encode a polypeptide having the amino acid sequence set forth in SEQ ID NO:1 (see FIG. 7). In accordance with another embodiment of the present invention, nucleic acids may include, but are not limited to, nucleic acids having substantially the same nucleotide sequence as nucleotides set forth in SEQ ID NO: 2 or SEQ ID NO:3 (FIG. 8 and FIG. 9, respectively). In accordance with a preferred embodiment, the nucleic acids of the present invention include the same nucleotide sequences as set forth in the SEQ ID NO:2 or 3. As used herein, the phrase "substantially the same nucleotide sequence" refers to DNA having sufficient homology to the reference polynucleotide, such that it will hybridize to the reference nucleotide under typical moderate stringency conditions. DNA having "substantially the same nucleotide sequence" as the reference nucleotide sequence has at least 60% homology with respect to the reference nucleotide sequence.

As used herein, the phrase "isolated" means a nucleic acid that is in a form that does not occur in nature. DNA sequences of the invention can be obtained by several methods. For example, the DNA can be isolated using hybridization techniques which are well known in the art. These include, but are not limited to: 1) hybridization of genomic or cDNA libraries with probes to detect homologous nucleotide sequences, 2) polymerase chain reaction (PCR) on genomic DNA or cDNA using primers capable of annealing to the DNA sequence of interest, and 3) antibody screening of expression libraries to detect cloned DNA fragments with shared structural features.

Preferably the polynucleotide of the invention is derived from a mammalian organism, and most preferably from a mouse, rat, or human. Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of an amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucl. Acid Res.*, 2:879, 1981).

The specific DNA sequences of the present invention can also be obtained by: 1) isolation of double-stranded DNA sequences from the genomic DNA; 2) chemical manufacture of a DNA sequence to provide the necessary codons for the polypeptide of interest; and 3) in vitro synthesis of a double-stranded DNA sequence by reverse transcription of mRNA isolated from an eukaryotic donor cell. In the latter case, a double-stranded DNA sequence by reverse transcription of mRNA isolated from an eukaryotic donor cell. In the latter case, a double-stranded DNA complement of mRNA is eventually formed which is generally referred to as cDNA. Of the three above-noted methods for developing specific DNA sequences for use in recombinant procedures, the isolation of genomic DNA isolates is the least common. This is especially true when it is desirable to obtain the microbial expression of mammalian polypeptides due to the presence of introns. The synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formation of plasmid or phage-carrying cDNA libraries which are derived from reverse transcription of mRNA, which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay, et al., *Nucl. Acid Res.*, 11:2325, 1983).

DNA sequences encoding TfR2 polypeptides can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell, since there may be mutations that occur during replication. However, such progeny are included when the term "host cell" is used. Methods of stable transfer, meaning that the foreign DNA is continuously maintained in the host, are known in the art.

In the present invention, the polynucleotide sequences may be inserted into a recombinant expression vector. The term "recombinant expression vector" refers to a plasmid, virus or other vehicle known in the art that has been manipulated by insertion of incorporation of the TfR2 genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to, the T7-based expression vector for expression in bacteria (Rosenberg, et al., *Gene,* 56:125, 1987), the pMSXND expression vector for expression in mammalian cells (Lee and Nathans, *J. Biol. Chem.,* 263:3521, 1988) and baculovirus-derived vectors for expression in insect cells. The DNA segment can be present in the vector operably linked to regulatory elements, for example, a promoter (e.g., T7, metallothionein 1, or polyhedrin promoters).

Polynucleotide sequences encoding TfR2 can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention.

Transformation of a host cell with recombinant DNA may be carried out by conventional techniques that are well known to those skilled in the art. Where the host is prokaryotic, such as *E. coli,* competent cells which are capable of DNA uptake can be prepared from cells harvested after an exponential growth phase and subsequently treated by the CaCl$_2$ method, using procedures well known in the art. Alternatively, MgCl$_2$ or RBCl can be used. Transformation can also be performed after forming a protoplast of the host cell, if desired.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be co-transformed with DNA sequences encoding TfR2 of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (See, for example, *Eukaryotic Viral Vectors,* Cold Spring Harbor Laboratory, Gluzman ed.k 1982).

Isolation and purification of microbial-expressed polypeptides, or fragments thereof, provided by the invention, may be carried out by conventional means including preparative chromatography and immunological separations involving monoclonal or polyclonal antibodies.

Another aspect of the present invention provides isolated TfR2 polypeptide, or fragments thereof, and functional equivalents thereof. As used herein, the term "isolated" means a protein molecule, free of cellular components, and/or contaminants normally associated with a native in vivo environment. The polypeptides of the present invention include any isolated naturally occurring allelic variant, as well as recombinant forms thereof.

Minor modifications of the primary amino acid of the peptide of the present invention may result in peptides which have substantially equivalent activity as compared with the specific peptide described herein. Such modifications may be deliberate, as by site-directed mutagenesis, or may be spontaneous. Modification may also be made to the length of the peptide of the present invention. It is recognized by those skilled in the art that it is possible that a peptide which is longer or shorter than the peptide of the present invention may still preserve substantially the same biological function of the peptide of the present invention. All of the peptides produced by these modifications are included herein as long as the biological activity of the peptides still exists.

The polypeptide of the present invention can be isolated using various methods well known to a person of skill in the art. The methods available for the isolation and purification of the polypeptides of the present invention include precipitation, gel filtration, ion-exchange, reverse-phase and affinity chromatography. Other well-known methods are described in Deutscher et al., *Guide to Protein Purification: Methods in Enzymology,* Vol. 182 (Academic Press, (1990)), which is incorporated herein by reference. Alternatively, the isolated polypeptides of the present invention can be obtained using well-known recombinant methods as described, for example, in the Examples.

An example of the means for preparing the invention polypeptides is to express nucleic acids encoding the TfR2 in a suitable host cell as described above. Polypeptides of the present invention can be isolated directly from cells that have been transformed with expression vectors. The polypeptide, biologically active fragments, and functional equivalents thereof can also be produced by chemical synthesis. For example, synthetic polypeptides can be produced using Applied Biosystems, Inc. Model 430A or 431A automatic peptide synthesizer (Foster City, Calif.), employing the chemistry provided by the manufacturer.

As used herein, the phrase "TfR2" refers to substantially pure native TfR2 proteins, or recombinantly expressed/produced proteins, including variants thereof encoded by mRNA, and generated by alternative splicing of a primary transcript, and further including fragments thereof which retain native biological activity. Preferred polypeptides of the present invention are those that contain substantially the same amino acid sequence set forth in SEQ ID NO:1 (FIG. 7). In accordance with one embodiment of the present invention, the isolated TfR2 polypeptide of the present invention is encoded by at least nucleotides set forth in SEQ ID NO:2 or SEQ ID NO:3 (See, FIG. 8 and FIG. 9, respectively). In accordance with one embodiment of the present invention, the sizes of the FLAG-tagged TfR2-α proteins are about 105 kDa in reducing condition, and about 215 kDa in non-reducing condition. The polypeptides of the present invention may be used to isolate ligands for transferrin receptors.

A further aspect of the present invention provides antibodies which are immunoreactive or bind to the peptides of the present invention. Antibodies which consist essentially of pooled monoclonal antibodies with different epitopic specificities, as well as distinct monoclonal antibody preparations, are provided. Monoclonal antibodies are made from antigen-containing peptides of the present invention or fragments by methods well known in the art (Kohler, et al., *Nature,* 256:495, 1975; *Current Protocols in Molecular Biology,* Ausubel et al., ed., 1989).

Antibodies which bind to the peptides of the present invention or a region of TfR2 represented by the peptides of the present invention can be prepared using an intact polypeptide or fragments containing peptides of interest as the immunizing antigen. A polypeptide or a peptide, such as Sequence ID No.1, used to immunize an animal can be derived from translated cDNA or chemical synthesis and is purified and conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

If desired, polyclonal antibodies can be further purified, for example, by binding to and eluting from a matrix to which a polypeptide or a peptide to which the antibodies were raised is bound. Those of skill in the art will know of various techniques common in the immunology arts for purification and/or concentration of polyclonal antibodies, as well as monoclonal antibodies. (See, for example, Coligan, et al., Unit 9, *Current Protocols In Immunology*, Wiley Interscience, 1991, incorporated by reference.)

The term "antibody" as used in this invention includes intact molecules as well as fragments thereof, such as Fab, Fab'$_2$ and Fv, which are capable of binding the epitopic determinant. These antibody fragments retain some ability to selectively bind with their antigen or receptor and are defined as follows:

(1) Fab, the fragment which contains a monovalent antigen-binding fragment of an antibody molecule, can be produced by digestion of a whole antibody with the enzyme papain to yield an intact light chain and a portion of one heavy chain;

(2) Fab'$_2$, the fragment of an antibody molecule, can be obtained by treating a whole antibody with pepsin, followed by reduction, to yield an intact light chain and a portion of the heavy chain; two Fab' fragments are obtained per antibody molecule;

(3) Fab'2, the fragment of the antibody that can be obtained by treating the whole antibody with the enzyme pepsin without subsequent reduction; Fab'$_2$ is a dimmer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. (See, for example, Harlow and Lane, *Antibodies: A Laboratory Manual*, Cold Spring Harbor Laboratory, New York (1988), incorporated herein by reference.)

As used in this invention, the term "determinant" means any antigenic determinant on an antigen to which the paratope of an antibody binds. Epitopic determinants usually consist of chemically active surface groupings of molecules, such as amino acids or sugar side chains, and usually have specific three-dimensional structural characteristics, as well as specific charge characteristics.

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody. Thus, in the present invention, an anti-idiotype antibody produced from an antibody which binds to, for example, the synthetic peptide of Sequence ID NO.1, can act as a competitive inhibitor for site on TfR2 which is required for iron metabolism in cells.

The antibodies of the present invention can be used to isolate the polypeptides of the present invention. Additionally, the antibodies are useful for detecting the presence of polypeptides of the present invention, as well as analysis of chromosome localization, and structural as well as functional domains.

Accordingly, another aspect of the present invention provides methods for detecting the presence of polypeptides of the present invention on the surface of a cell. The method comprises contacting the cell with an antibody that specifically binds to TfR2 polypeptides, under conditions permitting binding of the antibody to the polypeptides, detecting the presence of the antibody bound to the cell, and thereby detecting the presence of TfR2 polypeptides of the present invention on the surface of the cell. With respect to the detection of such polypeptides, the antibodies can be used for in vitro diagnostics or in vivo imaging methods.

Immunological procedures useful for in vitro detection of target TfR2 polypeptides in a sample include immunoassays that employ a detectable antibody; such immunoassays include, for example, ELISA, Pandex microfluorimetric assay, agglutination assays, flow cytometry, serum diagnostic assays and immunohistochemical staining procedures which are well known in the art. An antibody can be made detectable by various means well-known in the art. For example, a detectable marker can be directly or indirectly attached to the antibody; useful markers include, for example, radionucleotides, enzymes, fluorogens, chromogens and chemiluminescent labels.

Furthermore, the antibodies of the present invention can be used to modulate the activity of the TfR2 polypeptide in living animals, in humans, or in biological tissues or fluids isolated therefrom. Accordingly, the present invention provides compositions comprising a carrier and an amount of an antibody having specificity for TfR2 polypeptides effective to block binding of naturally occurring ligands to TfR2 polypeptides.

Another aspect of the present invention provides an antisense oligonucleotide capable of specifically binding to any portion of an mRNA that encodes TfR2 polypeptides so as to prevent or inhibit translation of the mRNA and inhibiting the translation of mRNA of TfR2 polypeptides. The antisense oligonucleotide may have a sequence capable of binding specifically with any portion of the sequence of the cDNA encoding TfR2 polypeptides. As used herein, the phrase "binding specifically" encompasses the ability of a nucleic acid sequence to form double-helical segments therewith via the formation of hydrogen bonds between the complementary base pairs. An example of an antisense oligonucleotide is an antisense oligonucleotide comprising chemical analogs of nucleotides.

In accordance with the present invention, it is provided compositions comprising an amount of the antisense oligonucleotide, described above, effective to reduce expression of TfR2 polypeptides by passing through a cell membrane and binding specifically with mRNA encoding TfR2 polypeptides so as to prevent translation and an acceptable hydrophobic carrier capable of passing through a cell membrane. Antisense oligonucleotide compositions are useful to inhibit translation of mRNA encoding TfR2 polypeptides. In accordance with one embodiment of the present invention, kits comprising the antisense of the present invention are also provided for inhibiting the expression of TfR2 polypeptides. In accordance with another embodiment of the present invention, the compositions may be used to modulate levels of expression of TfR2 polypeptides.

The present invention also provides compositions containing an acceptable carrier and any isolated, purified TfR2 polypeptide, an active fragment thereof, or a purified, mature protein and active fragments thereof, alone or in combination with each other. These polypeptides or proteins can be recombinantly derived, chemically synthesized or purified from native sources. As used herein, the term "acceptable carrier" encompasses any of the standard pharmaceutical carriers, such as phosphate buffered saline solution, water and emulsions such as an oil/water or water/oil emulsion, and various types of wetting agents.

EXAMPLES

Experimental Procedures

Cell Lines. HL-60, KG-1, U937 (myeloid leukemia); TF-1, K562 (erythroid leukemia); Jurkat, Molt-4 (T cell leukemia); Raji (Burkitt's lymphoma); LNCaP, PC-3 (prostate cancer); MCF-7, MDA-MB-231 (breast cancer); IMR-32 (neuroblastoma); SK-Hep1 (hepatoma); HepG2 (hepatoblastoma); U-2OS (osteosarcoma) and SW480 (colon cancer) cell lines were obtained from American Type Culture Collection (ATCC, Manassas, Va.). ML-1, NB4 and Kasumi 3 (myeloid leukemia), and both CHO-TRVb (TfR deficient Chinese hamster ovary) and TRVb-1 (human TfR stably transfected TRVb) cells were kindly provided by Drs. Minowada (14), Lanotte (15), Asou (16) and McGraw (17), respectively. Human mononuclear cells were isolated from the blood of a normal volunteer by centrifugation on a Ficoll-Paque (Pharmacia, Piscataway, N.J.) gradient at 400×g for 30 min. Informed consent was obtained from the individual.

Molecular Cloning of cDNA and genomic DNA. Complementary DNA libraries were constructed from TF-I and HL60 cells using a commercial kit (Marathon cDNA Amplification Kit, Clontech, Palo Alto, Calif.) and were used for 5'- and 3'-RACE reactions to obtain a full-length cDNA clone. Primers A and B (see Table 1) were used for 5'- and 3'-RACE, respectively. The products of RACE reactions were subcloned into the pGEM-Teasy vector (Promega, Madison, Wis.). We isolated two transcripts of 2.9 (α) and 2.5 (β) kb from the TF-I and HL60 cDNA libraries, respectively.

Genomic DNA was isolated from a human genomic library (Lambda FIX II Library, Stratagene, La Jolla, Calif.) using a 2.2 kbp fragment of the 3'-end of the TfR2 cDNA as a probe (shown as probe-I in FIG. 1). After restriction enzyme mapping, a 3.85 kb fragment which included exons 4–6 was subcloned into the pBluescript II(+) plasmid (Stratagene) (FIG. 1). Complementary and genomic DNA sequences were determined using an ABI Prism 373 automated sequencer (Perkin-Elmer, Foster City, Calif.).

Chromosomal Mapping. The GeneBridge 4 Radiation Hybrid Panel, RHO2 (Research Genetics, Huntsville, Ala.) was used to determine the chromosomal location of the TfR2 gene as previously described (18). The primers A and C amplified a 178 bp fragment located in exon 4 (FIG. 2). The PCR products were electrophoresed through a 1.5% agarose gel, Southern blotted and hybridized with a $^{32}$P-labeled probe of TfR2 (1 kbp fragment of the 5'-portion of the β form cDNA; shown as probe-2 in FIG. 1) to identify the hybrid clones containing the gene. The results were analyzed by accessing the database at the web site http://www-genome.wi.mit.edu/cgi-bin/contig/rhmapper.pl.

Northern Blot and RT-PCR Analyses. Northern blot and RT-PCR analyses were performed as previously described (18) with some modification. Human tissue Northern blot membranes and cDNAs were purchased from OriGene (Rockville, Md.). For Northern blot analysis, two TfR2 cDNA fragments (probe-1 and -2 as shown in FIG. 1), a human β-actin cDNA fragment (OriGene) and an approximately 300 bp TfR cDNA fragment were used as probes. For RT-PCR, the α form-specific primers (primers-A and -D) and the β form-specific primers (primers-C and -E) were used (Table 1 and FIG. 2). Conditions for amplification were 35 cycles of 94° C. for 30 s, 56° C. for 40 s and 72° C. for 1 min. As a control, glyceraldehyde-3-phosphate dehydrogenase (G3PDH) was amplified in a separate reaction using primers, 5'-CCATGGAGAAGGCTGGGG-3' and 5'-CAAAGTTGTCATGGATGACC-3' for 27 cycles. The product was electrophoresed through a 1.5% agarose gel, transferred to nylon membranes, hybridized with radiolabeled TfR2 and G3PDH probes and autoradiographed.

Transfection and Immunoblotting. CHO-TRVb cells were maintained in F12-nutrient mixture (Gibco-BRL) supplemented with 5% fetal bovine serum. An amino terminal FLAG-tagged TfR2-α cDNA was subcloned into pcDNA3 (Invitrogen, Carlsbad, Calif.). This plasmid (100 μg) was transfected into CHO-TRVb cells using Lipofectin (Gibco-BRL). For transient expression, cells were harvested 48 h after the transfection. We also isolated a stably expressing clone using G418 (200 μg/ml) selection and a standard limiting dilution method. The protein expression was confirmed by immunoblotting using anti-FLAG (M5) antibody

TABLE I

Primer Sequences for TfR2
These primers were used to amplify the TfR2 cDNAs in the RACE and RT-PCR analyses. Locations of these primers are shown as the nucleotide nunbers in the TfR2-α-transcript sequence (GenBank accession number AF067864). Also, the locations of primers A, C, D and E are shown in FIG. 2.

| Primer Name | Sequence | Direction | Location |
|---|---|---|---|
| A | 5'-CCACACGTGGTCCAGCTTCTGGCGGGAG-3' | Reverse | 603–576 |
| B | 5'-CAGTTGCATCATCAGGCCTTCC-3' | Forward | 1,061–1,082 |
| C | 5'-ACGTCTCTGGCATCCTTCC-3' | Forward | TfR2-β only |
| D | 5'-GTGGTCAGTGAGGATGTCAA-3' | Forward | 376–395 |
| E | 5'-TGTAGGGGCAGTAGACGTCA-3' | Reverse | 733–714 |

(Eastman Kodak, New Haven, Conn.). Immunoblot analysis was performed as previously described (19).

Flow Cytometric Analysis of Tf-binding to the Cell Surface. Approximately $3 \times 10^5$ cells were incubated with 5 μg/ml of biotinylated human holo-Tf (Sigma) in 500 μl MEM α media (GIBCO) either in the presence or absence of nonlabeled human holo-Tf (Sigma) or human Lf (Calbiochem, San Diego, Calif.) for 30 min on ice. After two washes with PBS supplemented with 0.1% bovine serum albumin, the cells were incubated with streptavidin-PE (DAKO). The cells were washed twice again and were subsequently analyzed by flow cytometry.

Analysis of Tf-mediated Iron Uptake. One milligram of human apo-Tf (Sigma) in 0.5 ml of 0.25 M Tris-HCl, 10 μM NaHCO3, pH 8.0 was mixed with 0.5 ml of 100 mM disodium nitrilotriacetate containing 0.4 mCi $^{55}FeCl_3$ (NEM, Boston, Mass.). The mixture was incubated at room temperature for 1 h and radiolabeled Tf was separated by filtration on a PD-10 column (Pharmacia). A specific activity of 27,000 cpm/μg was obtained. Cells were incubated with $^{55}$Fe-Tf in MEMα media in the presence or absence of 200-fold excess of nonlabeled holo-Tf at 37° C. with 5% $CO_2$. After washing with PBS, the cells were lysed with 0.1 N NaOH and the radioactivity was counted using a liquid scintillation counter.

Results

Molecular Cloning, Chromosomal Mapping and the Genomic Structure of the TfR2 Gene. We isolated seventeen 5'-RACE clones and ten 3'-RACE clones from the 7F-1 cDNA library. Assembly of their nucleotide sequences indicate an approximately 2.9 kb cDNA sequence (α form; GenBank accession number AF067864). Using 5' and 3' gene-specific primers, a cDNA clone encompassing the putative full-length coding sequence was created by PCR from the TF-1 cDNA library. This indicated that the predicted cDNA sequence belonged to an actual expressed mRNA. When we used a HL60 cDNA library for cloning TfR2, the 5'-RACE products were shorter than those from the TF-1 library, and the sequences around the 5'-end were different (β form). All 5'-RACE products from the TF-1 library belonged to the α form, and all 5'-RACE products from HL60 belonged to the β form.

FIG. 1 shows the map of the TfR2 gene. According to FIG. 1, an approximately 16 kbp genomic fragment was cloned from a human genomic library (genomic clone 1) and restriction enzyme sites were mapped. A 3.85 kbp fragment of the genomic clone 1 (shown as a shaded bar) was subcloned into the pBluescript II(+) plasmid and sequenced. The exon-intron borders shown in this figure were based on data deposited in the GenBank (accession number AP053356) with some modifications based on our data. The α transcript contains 18 exons (closed boxes on the line). The β transcript lacks exons 1–3, and has an additional 142 bases at the 5'-end of exon 4 (an open box on the line). The lower two boxes are the structures of the α and β transcripts. IC, TM and EC indicate the sequences encoding intracellular, transmembrane and extracellular domains, respectively. The locations of the probes that were used in the present invention are shown under the boxes.

According to the radiation hybrid panel analysis, TfR2 mapped on chromosome 7q22, between the D7S651 and WI-5853 markers. The restriction enzyme mapping and partial sequencing of a 16 kb genomic DNA clone and comparison with the deposited unpublished genomic sequence (20) revealed that the α form consisted of 18 exons (FIG. 1). However, some differences between their exon-intron borders and ours were noted. Our DNA sequence of the TfR2-α transcript contained an additional 81 nucleotides in exon 8 (nucleotides 1,053–1,133 in the TfR2-α transcript; GenBank accession number AF067864) and lacked 18 nucleotides in exon 18 (between nucleotides 2,163 and 2,164) as compared with their predicted mRNA sequence (20). This resulted in a twenty-seven amino acid addition and a six amino acid deletion for our predicted TfR2-α protein. Also, our mRNA sequence contained an additional 298 nucleotides in the 3'-untranslated region (UTR) (nucleotide 2580 to 2877).

The β form, which may be an alternative product of splicing or promoter usage, lacked exons 1, 2 and 3, and its first exon (exon 4 of the α form) had an additional 142 nucleotide bases at the 5'-end (FIGS. 1 and 2). FIG. 2 shows the DNA sequences of exons 3–5. Boxed sequences were found only in the β transcript. Arrows with solid and broken lines indicate the primer sequences used to synthesize the α and β transcripts, respectively, by RT-PCR. Putative translation initiation codon for the β transcript is shown as bold "ATG". Guanines at −3 and +4, which are consistent with Kozak's sequence for this initiation codon, are underlined.

The Primary Structure of TfR2 Proteins and mRNAs. The predicted amino acid sequence of TfR2-α is shown in FIG. 3. FIG. 3 shows the deduced amino acid sequence of TfR2-α-aligned with those for the human TfR and PSMA proteins. Identical residues are boxed. Hydrophobic amino acid stretches located in the putative transmembrane portions are shaded. The internalization motif of TfR and the correspondingly similar motif of TfR2-α are double underlined. Predicted initial methionine of TfR2-β is shown as a bold letter.

The hydrophobic stretch of residues from 81 to 104 following a pair of arginines represents the predicted transmembrane domain. It is located close to the amino terminus, similar to the transmembrane domains of TfR and PSMA (shaded section in FIG. 3)(10, 21). By analogy to TfR and PSMA, TfR2-α probably is a type II membrane protein. Therefore, residues 1 to 80 of TfR2-α may be the cytoplasmic domain and residues 105 to 801 the extracellular domain. In the extracellular domain, amino acid sequence homologies between TfR2-α and either TfR or PSMA were quite high. The extracellular domain of TfR2-α was 45% identical and 66% similar with that of TfR. With PSMA, the identity was 27% and the similarity 60%. The cysteine residues at positions 89 and 98 of TfR form disulfide bonds resulting in homodimerization. Two cysteine residues at positions 108 and 111 in TfR2-α are located in an analogous region and may serve a similar function. In addition, TfR2-α contains the motif YQRV (amino acid 23–26) in the middle of the cytoplasmic domain, that may function as an internalization signal, similar to the YTRF motif in TfR (FIG. 3, double underlined)(22–24).

The β transcript lacks exons 1 to 3, which encode the entire transmembrane and cytoplasmic domains as well as part of the extracellular domain including the two cysteine residues at 108 and 111. The additional 142 nucleotide 5'-sequence in exon 4 does not contain an initiation codon. Translation probably starts at the ATG located at nucleotide 542, which is in frame with the α transcript ORF. The predicted initial methionine is shown in FIG. 2, exon 4 and FIG. 3 as bold "ATG" and "M", respectively. This ATG contains a G at positions −3 and +4 indicating it is an ideal start site for translation (25). Hence the predicted protein product of the β transcript would lack both a transmembrane domain and signal peptide, resulting in a possible intracellular protein that may or may not be functional.

Although the primary structure of the TfR2-α protein seemed to be quite similar to TfR, the 3'-UTR of the TfR2 mRNA was shorter than that of the TfR transcript. Also, a typical iron-responsive element (IRE) was not present in the UTRs of either of the TfR2 transcripts (26).

Figure 4A:
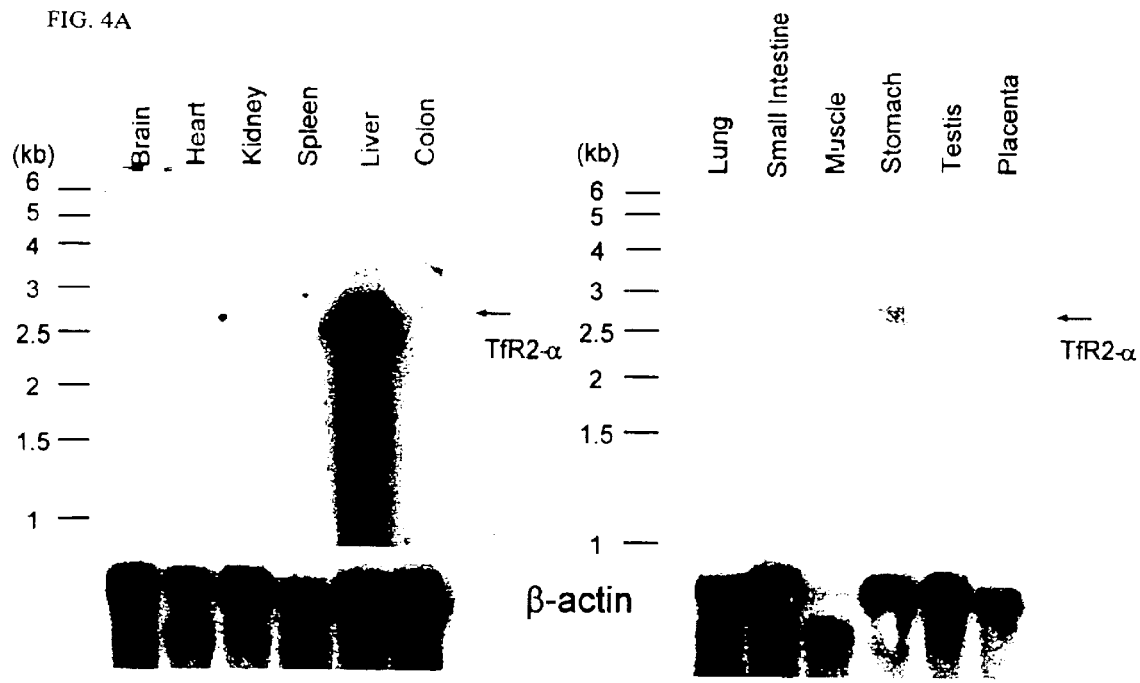
FIGS. 4A and 4B show the results of Northern blot analysis on multiple tissue blots of human mRNA (A), and cell line blots of total RNA (B).
Figure 4B:
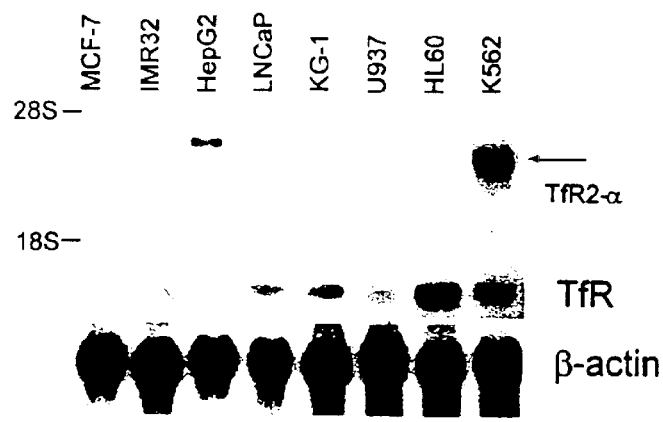

Characterization of TfR2 mRNA Expression. FIGS. 4A and 4B show the results of the Northern blot analysis of poly A+ RNA from human tissues. Hybridization was with $^{32}$P- labeled TfR2 probes. FIG. 4A shows multiple tissue blots of human mRNA were hybridized with a TfR2 probe (probe No. 1 in FIG. 1). Membranes were hybridized in the same bottle at the same time, and the autoradiograms were developed after a 12 hr exposure. In FIG. 4B, thirty micrograms of total RNA from cell lines were loaded in each lane and hybridized with a TfR2 probe (probe No. 2) and a TfR probe. A $^{32}$P-labeled P-actin probe was used as a control for all blots. Molecular weight markers or the positions of ribosomal RNA are indicated on the left.

Northern blot analysis of poly A+ RNA from human tissues showed that a 2.9 kb mRNA for TfR2 was expressed predominantly in the liver and, to a lesser degree, in the stomach (FIG. 4A). This corresponded with the length of TfR2-α cDNA isolated from TF-1 cells. In addition, faint bands at 4 kb (stomach) and 1.7 kb (liver, lung, small intestine, stomach, testis and placenta) were observed. These bands may reflect the presence of additional alternative forms of TfR2 mRNA. Northern blot analysis of total RNA of various cell lines revealed a high expression of TfR2-α in K562 (erythroleukemia) and HepG2 (hepatoblastoma) (FIG. 4B). The expression levels of TfR2-α were not always correlated with those of TfR (FIG. 4B). No transcripts corresponding to TfR2-β (2.5 kb) were observed by Northern blot analysis.

Figures 5A, 5B:
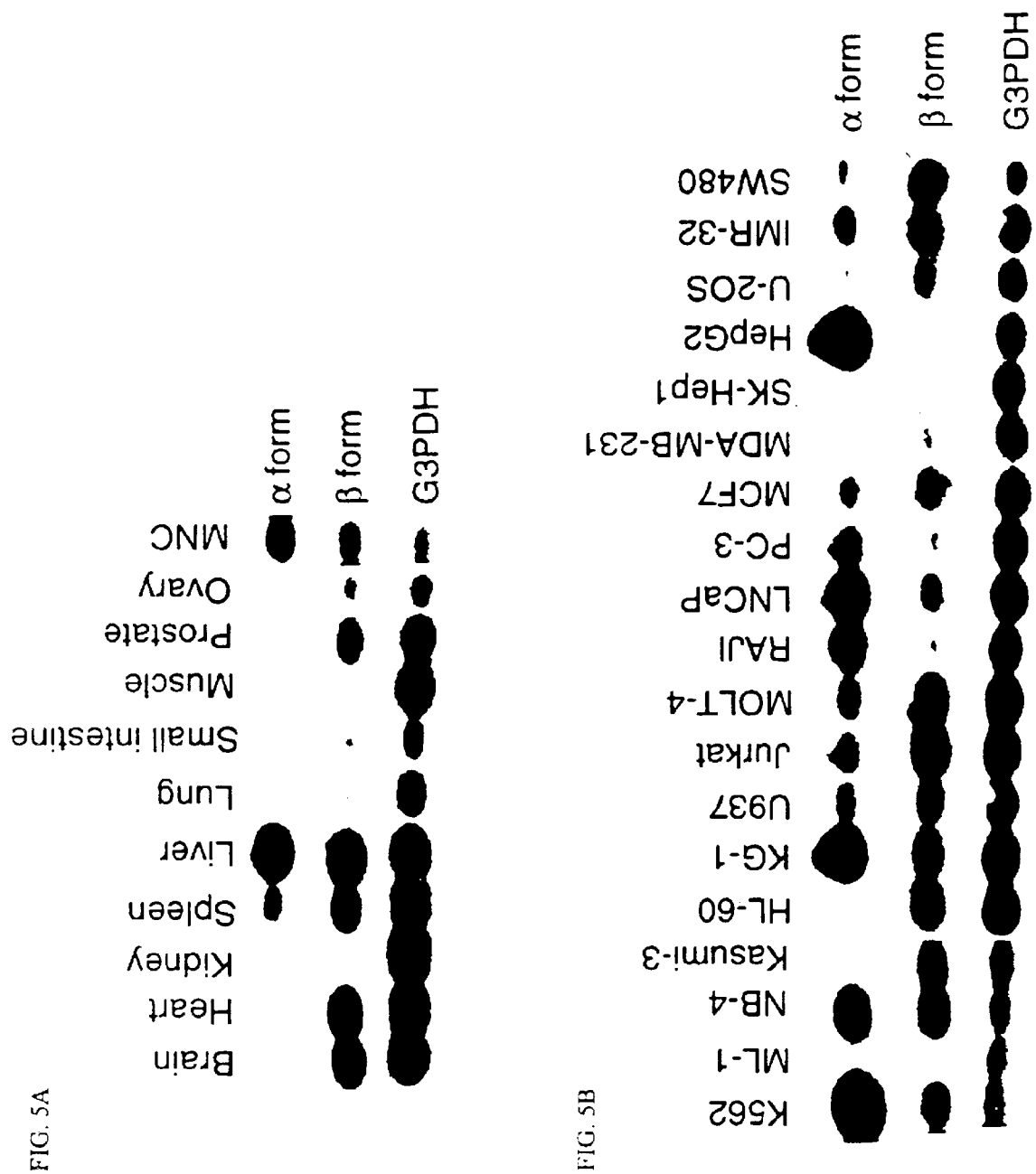
FIGS. 5A and 5B show the representative results of RT-PCR analyses performed with primers for α and β transcripts of TfR2 (35 cycles) as well as G3PDH (27 cycles).

To compare the expression of the α and β transcripts, RT-PCR was performed using specific primers for each form. FIGS. 5A and 5B show the representative results of RT-PCR analyses. RT-PCRs were performed with primers for α and β transcripts of TfR2 (35 cycles) as well as G3PDH (27 cycles). The products were electrophoresed through 1.5% agarose gels, transferred to nylon membranes, hybridized with radiolabeled probes and autoradiographed. FIG. 5A shows cDNA panels of human tissues. (MNC; human peripheral blood mononuclear cells.) FIG. 5B shows cDNAs from various human cell lines. Experiments were repeated at least twice for each sample, and the figures are representative results. The cDNAs for ML-1, Kasumi-3, HL60 and MDA-MB-231 are negative, but showed trace levels of α form expression in other experiments.

FIGS. 5A and 5B show that using a human tissue cDNA panel as a template, the expression of the α form was limited to the liver, spleen, lung, muscle, prostate and peripheral blood mononuclear cells (FIG. 5A). On the other hand, expression of the β form occurred in all of the human tissues tested. Human cancer cell lines from various tissues were studied for expression of the two transcripts. Most of the cell lines expressed both transcripts except three; SK-Hep1 (hepatoma) lacked both α and β transcripts, HepG-2 (hepatoblastoma) and ML-I (myeloblast) lacked the β transcript (FIG. 5B). Neither deletion nor rearrangement of the TfR2 gene was detected in Southern blot analysis in SK-Hep1 (data not shown).

Figure 6C:
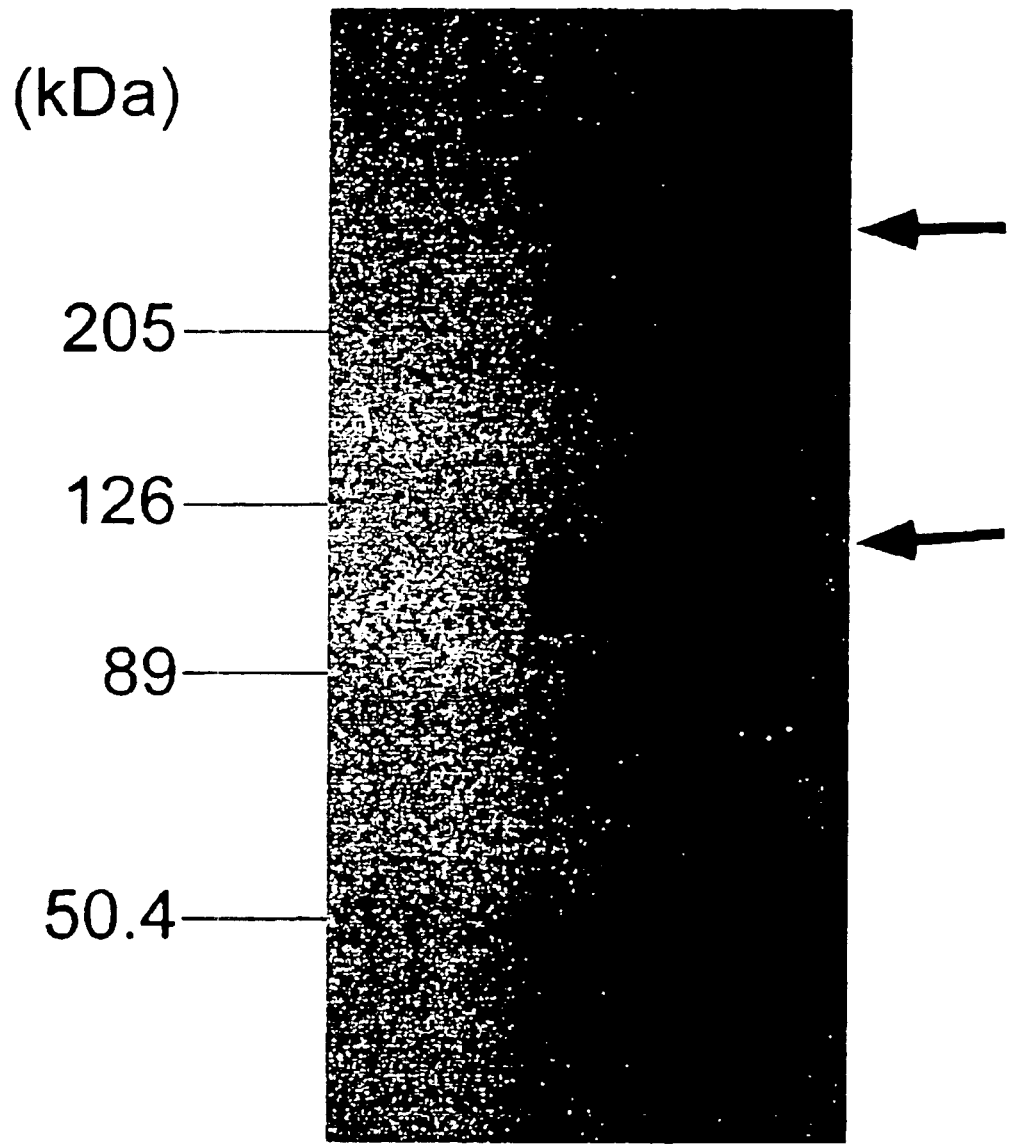

Tf-binding to the TfR2-α Transfected Cells. To analyze the function of TfR2-α, we stably transfected CHO-TRVb cells, which lack functional TfR, with FLAG-tagged TfR2-α. FIGS. 6A, 6B and 6C show the expression and functional analysis of TfR2-α protein. In FIG. 6A, Tf-binding to the cell surface was examined in neomycin resistant control CHO-TRVb cells (left panels), FLAG-tagged TfR2-α stably transfected cells (middle) and TRVb-1,TfR stably transfected cells (right). The cells were incubated with 5 μg/ml of biotinylated human holo-Tf in MEM a media for 30 min on ice. After washing with PBS, the cells were incubated with streptavidin-PE, and analyzed by flow cytometry. The solid lines show the histograms without competition. Competition experiments were performed in the presence of either 10-fold (----) or 100-fold (------) excess of either nonlabeled Tf (upper panels) or Lf (lower panels). In FIG. 6B, Tf-mediated $^{55}$Fe uptake was examined in neomycin resistant control CHO-TRVb cells (Neo cells), human TfR stably transfected cells (TfR cells) and FLAG-tagged TfR2-α stably transfected cells (TfR2 cells). Closed symbols (-C) represent cold competition experiments with 200-fold excess of nonlabeled Tf. The mean ±S. D. from either quadruplicate (without competition) or triplicate (cold competition) experiments is shown. In FIG. 6C, cell lysates from pcDNA3 transiently transfected cells (lane 1) and FLAG-tagged TfR2 transfected cells (lanes 2 and 3) were electrophoresed through a 4–15% linear gradient SDS-polyacrylamide gel. For the sample in lane 3,2-mercaptoethanol was omitted from the sample buffer. After transferring to a PVDF membrane, FLAG-fusion proteins were detected by immunoblotting. The positions of molecular weight markers are indicated on the left.

In FIGS. 6A, 6B and 6C, the cell surface Tf-binding was examined using biotinylated Tf and flow cytometry. Neomycin resistant control cells were almost negative for the cell surface Tf-binding (FIG. 6A, left). TRVb-1, the human TfR stably transfected cells were positive for cell surface binding of Tf, and this binding was competed by nonlabeled Tf but not by Lf (FIG. 6A, middle). For the CHO-TRVb cells stably expressing TfR2-α, the mean level of cell surface Tf-binding was clearly higher than that of the control cells (FIG. 6A, right, solid lines). In competition experiments, 10-fold excess of nonlabeled Tf markedly inhibited the binding of biotinylated Tf, but even 100-fold excess of Lf did not inhibit the binding (FIG. 6A, right, broken lines). Tf-binding to the TfR2-α cells was also examined in a transient expression system using CHO-TRVb cells, and the levels of Tf-binding to the cell surface were consistently as follows: TfR cells>TfR2-α cells>pcDNA3 cells (data not shown).

Tf-mediated $^{55}$Fe Uptake of the TfR2-α-Transfected Cells. Human TfR and TfR2-α stably transfected CHO-TRVb cells were incubated with $^{55}$Fe-Tf, and $^{55}$Fe uptake was measured. Neomycin resistant CHO-TRVb cells were used as controls. Tf-mediated $^{55}$Fe uptake by the TfR2-α cells was comparable to TfR cells; both were clearly higher than control cells (FIG. 6B). Competition by 200-fold excess of nonlabeled Tf almost completely blocked $^{55}$Fe incorporation in these three cell lines after a 5 h incubation (FIG. 6B). In spite of the absence of functional TfR, a slight uptake of Tf-mediated $^{55}$Fe was also observed in the control TRVb cells as previously reported by Chan, et al. (27).

Dimerization of the FLAG-tagged TfR2-α Proteins Expressed in Mammalian Cells. Cell lysates from the cells transiently transfected with pcDNA3 empty vector or the FLAG-tagged TfR2-α plasmid were examined by immunoblotting using anti-FLAG antibody (FIG. 6C). Two closely migrated bands of 105 kDa were observed in the cell lysate transfected with FLAG-tagged TfR2-α under reducing conditions (lane 2). When 2-mercaptoethanol was omitted from the sample loading buffer, the doublet of 105 kDa decreased, but a protein of ~215 kDa appeared (lane 3). Faint bands of ~260 kDa and ~125 kDa were also seen under non-reducing conditions (lane 3, arrows).

Discussion

The primary structure of the TfR2-α protein deduced from its mRNA is similar to that of TfR (see RESULTS). In addition, TfR2-α transfected cells showed increases of both Tf-binding and Tf-mediated iron uptake (FIGS. 6A and B).

However, the mechanisms that regulate expression of TfR2 and TfR may be different. Levels of the TfR protein are regulated post-transcriptionally through IREs in its 3'-UTR, to which iron regulatory protein-I (IRP-1) and IRP-2 can bind. In cells lacking sufficient iron, IRPs bind to the iron-responsive elements of TfR mRNA and stabilize these transcripts. In the presence of excess intracellular iron, IRPs are released, leading to degradation of the TfR mRNA. In rapidly growing cells, proto-oncogene c-MYC represses H-ferritin and upregulated IRP-2, and the upregulation of IRP-2 may increase TfR protein expression (28). Neither the 3'- nor the 5'-UTRs of the TfR2 mRNAs have a detectable IRE-like structure, suggesting another mechanism(s) may regulate TfR2 expression.

Northern blot analysis using normal human poly A+ RNA from a variety of tissues showed that the liver was the only cell type that prominently expressed TfR2-α (FIG. 4A). Also, TfR2-α was expressed highly in the K562 erythroleukemic cell line which is capable of hemoglobin synthesis (FIG. 4B). This result suggests that erythroid hematopoietic cells may also express high levels of TfR2-α. The major product of red blood cells is hemoglobin which contains abundant iron, and if TfR2-α is involved in iron transport, it would be expected to be strongly expressed on these cells. In erythroid cells, Cotner et al. predicted the presence of an alternative form of TfR using a set of monoclonal antibodies against TfR (29). Their findings may be ascribed to TfR2-α.

The size of the FLAG-tagged TfR2-α expressed in mammalian cells is ~105 kDa in the presence of a reducing agent, and is ~215 kDa in the absence of a reducing agent (FIG. 6C), indicating dimerization of TfR2-α through disulfide bonds. The size of FLAG-tagged TfR2-α monomer, ~105 kDa, is larger than the molecular weight calculated from the amino acid sequence (~90 kDa). This may reflect post-translational modifications of the protein such as glycosylation. Actually there are 4 putative N-glycosylation sites (amino acids 240–243, 339–342, 540–543 and 754–757) in the TfR2-α protein. Hence, the double bands of ~105 kDa seen in FIG. 6C may be due to different states of glycosylation. In addition, faint bands of ~260 kDa and ~125 kDa just above the clear bands of ~215 kDa and ~105 kDa, respectively, were observed under non-reducing conditions (FIG. 6C, lane 3, arrows). These faint bands may reflect interaction of TfR2-α with a small protein (~20 kDa) through disulfide bonds, which may or may not be a ligand.

To investigate the function of TfR2, Tf and other Tf family members were considered as candidate ligands of TfR2. Six members of Tf family have been cloned to date; Tf, Lf, melanotransferrin (30), ovotransferrin, saxiphilin (31), and porcine inhibitor of carbonic anhydrase (32). The last two do not possess iron-binding properties and the last three have not been identified in humans. Melanotransferrin is an unlikely TfR2 ligand because it is a membrane-bound protein of melanoma cells. Only Tf and Lf remained as candidates. The CHO-TRVb cells transfected with FLAG-tagged TfR2-α showed higher levels of Tf-binding to the cell surface than did the control cells (FIG. 6A). This indicates that FLAG-tagged TfR2-α was expressed on the cell surface and was bound by Tf. This binding was effectively competed by nonlabeled Tf but not by Lf (FIG. 6A). This indicates that Tf can bind to TfR2-α more specifically than can Lf. In addition, Tf-mediated iron uptake by TfR2-α transfected cells was obviously higher than that of control cells (FIG. 6B).

However, if the only ligand for TfR2-α is Tf and the main function of TfR2-α is cellular iron uptake, why do the cells have two different receptors for Tf? TfR2-α may simply be another transferrin receptor with a different affinity. Possibly, the fate of the Tf/TfR2-α complex on the cell surface may be different from that of the Tf/TfR complex. The putative internalization motif of TfR2-α is not identical to that of TfR, and even a minor difference of the internalization motif may result in different destinations of the endosomes (24). Still, the possibility that TfR2-α has another specific ligand other than Tf remains. Recently, the field of iron metabolism has been markedly advanced by the discoveries of HFE, mutations of which occur in most of the patients with hereditary hemochromatosis (8, 9), and Nramp2, an intestinal iron transporter (33, 34). Does TfR2-α-a bind to HFE, which normally forms a complex with TfR on the cell membrane? If it does, TfR2-α may affect the cellular iron uptake by chelating HFE. Can TfR2-α form a heterodimer with TfR? This may also affect cellular iron uptake. Elucidation of the precise role of TfR2 may provide an important step for clarifying the mechanisms and the regulation of cellular iron uptake.

We cloned two different forms of transcripts from TfR2 gene, α and β. Two different transcripts are also expressed from the PSMA gene, another member of the TfR-like family. The shorter form of PSMA lacks the 5'-end encoding the transmembrane domain (35), similar to the β-form of TfR2. Nearly a 100-fold difference in the ratio of expression of the longer and the shorter forms of PSMA mRNA has been reported during progression of prostate cancer, with the shorter form predominant in normal cells and the longer form predominant in the cancer cells (36). Using the extremely sensitive RT-PCR method, we could distinguish expression of the (α and β forms of the TfR2 gene. Among normal tissues, the expression of the α (longer) form was detected in the liver, spleen, lung, muscle, prostate and peripheral blood mononuclear cells (FIG. 5A). The β form was distributed more widely. Interestingly, the two cell lines derived from the liver (SK-Hep1 and HepG2) lacked expression of the β form, whereas most cell lines from other tissues as well as normal liver expressed this shorter form (FIGS. 5A and 5B).

We mapped TfR2 to chromosome 7q22. Deletion or loss of heterozygosity of this chromosomal region has been reported in several malignant diseases including myelodysplastic syndromes, acute myeloid leukemia, as well as breast, ovarian and pancreatic cancers (37–41). It is speculated that TfR2 mutations may occur in these cancers.

REFERENCES

1. Richardson, D. R. and Ponka, P. (1997) *Biochim. Biophys. Acta* 1331, 140.
2. Testa, U., Pelosi, E. and Peschle, C. (1993) *Crit. Rev. Oncog.* 4, 241–276.
3. Lash, A. and Saleem, A. (1995) *Ann. Clin. Lab. Sci.* 25, 20–30.
4. Kauppi, B., Nielsen, B. B., Ramaswamy, S., Larsen, I. K., Thelander, M., Thelander, L. and Eklund, H. (1996) *J. Mol. Biol.* 262, 706–720.
5. Miskimins, W. K., McClelland, A., Roberts, M. P. and Ruddle, F. H. (1986) *J. Cell Biol.* 103, 1781–1788.
6. Gross, S., Helm, K., Gruntmeir, J. J., Stillman, W. S., Pyatt, D. W. and Irons, R. D. (1977) *Eur. J. Haematol.* 59, 318–326.
7. Gatter, K. C., Brown, G., Trowbridge, I. S., Woolston, R. E. and Mason, D. Y. (1983) *J. Clin. Pathol.* 36, 539–545.
8. Feder, J. N., Gnirke, A., Thomas, W., Tsuchihashi, Z., Ruddy, D. A., Basava, A., Dormishian, F., Domingo, R. J., Ellis, M. C., Fullan, A., Hinton, L. M., Jones, N. L., Kimmel, B. E., Kronmal, G. S., Lauer, P., Lee, V. K., Loeb, D. B., Mapa, F. A., McClelland, E., Meyer, N. C., Mintier, G. A., Moeller, N., Moore, T., Morikang, E., Prass, C. E., Quintana, L., Starnes, S. M., Schatzman, R. C., Brunke, K. J., Drayna, D. T., Risch, N. J., Bacon, B. R. and Wolff, R. K. (1996) *Nature Genet.* 13, 399–408.

9. Feder, J. N., Penny, D. M., Irrinki, A., Lee, V. K., Lebron, J. A., Watson, N., Tsuchihashi, Z., Sigal, E., Bjorkman, P. J. and Schatzman, R. C. (1998) *Proc. Natl. Acad. Sci. US.A.* 95, 1472–1477.

10. Israeli, R. S., Powell, T., Fair, W. R. and Heston, W. D. W. (1993) *Cancer Res.* 53, 11. Carter, R. E., Feldman, A. R. and Coyle, J. T. (1996) *Proc. Natl. Acad. Sci. U.S.A.* 93, 749–753.

12. Gregorakis, A. K., Holmes, E. H. and Murphy, G. P. (1998) *Semin. Urol. Oncol.* 16, 2–12.

13. Heston, W. D. W. (1998) *Urology* 49, 104–112.

14. Fukuda, M., Koeffler, H. P. and Minowada, J. (1981) *Proc. Natl. Acad Sc. U.S.A.* 78, 6299–6303.

15. Lanotte, M., Martin-Thouvenin, V., Najman, S., Balerini, P., Valenisi, F. and Berger, R. (1991) *Blood* 77, 1080–1086.

16. Asou, H., Suzukawa, K., Kita, K., K., N., Ueda, H., Morishita, K. and Kamada, N. (1996) *Jap. J. Cancer Res.* 87, 269–274.

17. McGraw, T. E., Greenfield, L. and Maxfield, F. R. (1987) *J. Cell Biol.* 105, 207–214.

18. Yang, R., Morosefti, R. and Koeffler, H. P. (1997) *Cancer Res.* 57, 913–920.

19. Chumakov, A. M., Grillier, I., Chumakova, E., Chih, D., Slater, J. and Koeffler, H. P. (1997) *Mol. Cell Biol.* 17, 1375–1386.

20. Gleockner, G., Rosenthal, A., Scherer, S., Weber, J., Schattevoy, R. and Tsui, L. (1998) *Homo sapiens* chromosome 7q22 sequence, complete sequence. GenBank accession number AP053356.

21. Schneider, C., Owen, M. J., Banville, D. and Williams, J. G. (1984) *Nature* 311, 675–678.

22. Collawn, J. F., Stangel, M., Kuhn, L. A., Esekogwu, V., Jing, S., Trowbridge, I. S. and Tainer, J. A. (1990) *Cell* 83, 1061–1072.

23. Jing, S. Q., Spencer, T., Miller, K., Hopkins, C. and Trowbridge, 1. S. (1990) *J. Cell Biol.* 283–294.

24. Johnson, A. O., Ghosh, R. N., Dunn, K. W., Garippa, R., Park, J., Mayor, S., Maxfield, F. R. and McGraw, T. E. (1996) *J. Cell Biol.* 135, 1749–1762.

25. Kozak, M. (1981) *Nuc. Acids Res.* 9, 5233–5262.

26. Leibold, E. A., Laudano, A. and Yu, Y (1990) *Nuc. Acids Res.* 18, 1819–1824.

27. Chan, R. Y. Y., Ponka, P. and Schulman, H. M. (1992) *Exp. Cell Res.* 202, 326–336.

28. Wu, K., Polack, A. and Dalla-Favera, R. (1999) *Science* 283, 676–679.

29. Cotner, T., Gupta, A. D., Papayannopoulou, T. and Stamatoyannopoulos, G. (1989) *Blood* 73, 214–221.

30. Rose, T. M., Plowman, G. D., Teplow, D. B., Dreyer, W. J., Hellstrom, K. E. and Brown, J. P. (1986) *Proc. Natl. Acad. Sci. U.S.A.* 83, 1261–1265.

31. Llewellyn, L. E. and Moczydlowski, E. G. (1994) *Biochem.* 33, 12312–12322.

32. Wuebbens, M. W., Roush, E. D., Decastro, C. M. and Fierke, C. A. (1997) *Biochem.* 36, 4327–4336.

33. Fleming, M. D., Trenor, C. C. I., Su, M. A., Foernzler, D., Beier, D. R., F., D. W. and Andrews, N. C. (1997) *Nat Genet.* 16, 383–386.

34. Gunshin, H., Mackenzie, B., Berger, U. V., Gunshin, Y., Romero, M. F., Boron, W. F., Nussberger, S., Gollan, J. L. and Hediger, M. A. (1997) *Nature* 388, 482.

35. Su, S. L., Huang, I. P., Fair, W. R., Powell, C. T. and Heston, W. D. (1995) *Cancer Res.* 55, 1441–1443.

36. Weissensteiner, T. (1998) *Nuc. Acids Res.* 26, 687.

37. Johnson, E. and Cotter, F. E. (1997) *Blood Rev.* 11, 46–55.

38. Liang, H., Fairman, J., Claxton, D. F., Nowell, P. C., Green, E. D. and Nagarajan, L. (1998) *Proc. Natl. Acad. Sci. U.S.A.* 95, 3781–3785.

39. Kristjansson, A. K., Eiriksdottir, G., Ragnarsson, G., Sigurdsson, A., Gudmundsson, J., Barkardottir, R. B., Jonasson, J. G., Egilsson, V. and Ingvarsson, S. (1997) *Anticancer Res.* 17, 93–98.

40. Kerr, J., Leary, J. A., Hurst, T., Shih, Y. C., Antalis, T. M., Friedlander, M., Crawford, E., Khoo, S. K., Ward, B. and Chenevix-Trench, G. (1996) *Oncogene* 13, 815–818.

41. Achille, A., Biasi, M. O., Zamboni, G., Bogina, G., Magalini, A. R., Pederzoli, P., Perucho, M. and Scarpa, A. (1996) *Cancer Res.* 56, 3808–3813.

What is claimed is:

1. An isolated nucleic acid molecule comprising a nucleic acid encoding a polypeptide having a sequence selected from the group consisting of:
   (a) the amino acid sequence of SEQ ID NO: 1;
   (b) an amino acid sequence encoded by the nucleic acid sequence of SEQ ID NO: 2;
   (c) an amino acid sequence encoded by the nucleic acid sequence of SEQ ID NO: 3.

2. The isolated nucleic acid molecule of claim 1, wherein the sequence is (a).

3. The isolated nucleic acid molecule of claim 2, wherein the sequence is (b).

4. The isolated nucleic acid molecule of claim 2, wherein the sequence is (c).

5. The isolated nucleic acid molecule of claim 2, wherein the nucleic acid molecule comprises a molecule selected from the group consisting of DNA, cDNA, and RNA.

6. A recombinant expression vector comprising DNA of claim 5.

7. An isolated host cell comprising the vector of claim 6, wherein the cell is selected from the group consisting of a prokaryotic cell and a eukaryotic cell.

8. The host cell of claim 7, wherein the cell expresses a polypeptide having a sequence selected from the group consisting of:
   (a) the amino acid sequence of SEQ ID NO: 1;
   (b) an amino acid sequence encoded by the nucleic acid sequence of SEQ ID NO: 2;
   (c) an amino acid sequence encoded by the nucleic acid sequence of SEQ ID NO: 3.

9. The host cell of claim 8, wherein the sequence is (a).

10. The host cell of claim 8, wherein the sequence is (b).

11. The host cell of claim 8, wherein the sequence is (c).

12. The vector of claim 6, wherein the vector is selected from the group consisting of a plasmid and a virus.

13. The vector of claim 6, wherein the vector is a virus selected from the group consisting of simian virus 40 and bovine papilloma virus.

14. An isolated host cell comprising the vector of claim 6, wherein the cell is selected from the group consisting of a bacterial cell, a yeast cell, an insect cell, and a mammalian cell.

15. The host cell of claim 8, wherein the vector is selected from the group consisting of a T7-based expression vector for expression in bacteria, a baculovirus-derived vector for expression in insect cells, and a pMSXND expression vector for expression in mammalian cells.

16. Isolated mRNA complementary to the DNA of claim 5.

17. An isolated host cell comprising nucleic acid of claim 1, wherein the nucleic acid is operatively associated with a regulatory sequence that controls gene expression.

18. The isolated host cell of claim 17, wherein the regulatory sequence is a promoter.

19. The isolated host cell of claim 18, wherein the promoter is selected from the group consisting of T7, metallothionein I, and polyhedrin promoters.

* * * * *

SEQUENCE LISTING

<160> NUMBER OF SEQ ID NOS: 3

<210> SEQ ID NO 1
<211> LENGTH: 801
<212> TYPE: PRT
<213> ORGANISM: human cells

<400> SEQUENCE: 1

Met Glu Arg Leu Trp Gly Leu Phe Gln Arg Ala Gln Gln Leu Ser Pro
 1               5                  10                  15

Arg Ser Ser Gln Thr Val Tyr Gln Arg Val Glu Gly Pro Arg Lys Gly
            20                  25                  30

His Leu Glu Glu Glu Glu Asp Gly Glu Glu Gly Ala Glu Thr Leu
        35                  40                  45

Ala His Phe Cys Pro Met Glu Leu Arg Gly Pro Glu Pro Leu Gly Ser
    50                  55                  60

-continued

```
Arg Pro Arg Gln Pro Asn Leu Ile Pro Trp Ala Ala Gly Arg Arg
 65                  70                  75                  80

Ala Ala Pro Tyr Leu Val Leu Thr Ala Leu Leu Ile Phe Thr Gly Ala
             85                  90                  95

Phe Leu Leu Gly Tyr Val Ala Phe Arg Gly Ser Cys Gln Ala Cys Gly
            100                 105                 110

Asp Ser Val Leu Val Ser Glu Asp Val Asn Tyr Glu Pro Asp Leu
            115                 120                 125

Asp Phe His Gln Gly Arg Leu Tyr Trp Ser Asp Leu Gln Ala Met Phe
        130                 135                 140

Leu Gln Phe Leu Gly Glu Gly Arg Leu Glu Asp Thr Ile Arg Gln Thr
145                 150                 155                 160

Ser Leu Arg Glu Arg Val Ala Gly Ser Ala Gly Met Ala Ala Leu Thr
                165                 170                 175

Gln Asp Ile Arg Ala Ala Leu Ser Arg Gln Lys Leu Asp His Val Trp
            180                 185                 190

Thr Asp Thr His Tyr Val Gly Leu Gln Phe Pro Asp Pro Ala His Pro
        195                 200                 205

Asn Thr Leu His Trp Val Asp Glu Ala Gly Lys Val Gly Glu Gln Leu
    210                 215                 220

Pro Leu Glu Asp Pro Asp Val Tyr Cys Pro Tyr Ser Ala Ile Gly Asn
225                 230                 235                 240

Val Thr Gly Glu Leu Val Tyr Ala His Tyr Gly Arg Pro Glu Asp Leu
                245                 250                 255

Gln Asp Leu Arg Ala Arg Gly Val Asp Pro Val Gly Arg Leu Leu Leu
            260                 265                 270

Val Arg Val Gly Val Ile Ser Phe Ala Gln Lys Val Thr Asn Ala Gln
        275                 280                 285

Asp Phe Gly Ala Gln Gly Val Leu Ile Tyr Pro Glu Pro Ala Asp Phe
    290                 295                 300

Ser Gln Asp Pro Pro Lys Pro Ser Leu Ser Ser Gln Ala Val Tyr
305                 310                 315                 320

Gly His Val His Leu Gly Thr Gly Asp Pro Tyr Thr Pro Gly Phe Pro
                325                 330                 335

Ser Phe Asn Gln Thr Gln Phe Pro Pro Val Ala Ser Ser Gly Leu Pro
            340                 345                 350

Ser Ile Pro Ala Gln Pro Ile Ser Ala Asp Ile Ala Ser Arg Leu Leu
        355                 360                 365

Arg Lys Leu Lys Gly Pro Val Ala Pro Gln Glu Trp Gln Gly Ser Leu
370                 375                 380

Leu Gly Ser Pro Tyr His Leu Gly Pro Gly Pro Arg Leu Arg Leu Val
385                 390                 395                 400

Val Asn Asn His Arg Thr Ser Thr Pro Ile Asn Asn Ile Phe Gly Cys
                405                 410                 415

Ile Glu Gly Arg Ser Glu Pro Asp His Tyr Val Val Ile Gly Ala Gln
            420                 425                 430

Arg Asp Ala Trp Gly Pro Gly Ala Ala Lys Ser Ala Val Gly Thr Ala
        435                 440                 445

Ile Leu Leu Glu Leu Val Arg Thr Phe Ser Ser Met Val Ser Asn Gly
    450                 455                 460

Phe Arg Pro Arg Arg Ser Leu Leu Phe Ile Ser Trp Asp Gly Gly Asp
465                 470                 475                 480
```

```
Phe Gly Ser Val Gly Ser Thr Glu Trp Leu Glu Gly Tyr Leu Ser Val
                485                 490                 495
Leu His Leu Lys Ala Val Val Tyr Val Ser Leu Asp Asn Ala Val Leu
                500                 505                 510
Gly Asp Asp Lys Phe His Ala Lys Thr Ser Pro Leu Leu Thr Ser Leu
                515                 520                 525
Ile Glu Ser Val Leu Lys Gln Val Asp Ser Pro Asn His Ser Gly Gln
            530                 535                 540
Thr Leu Tyr Glu Gln Val Val Phe Thr Asn Pro Ser Trp Asp Ala Glu
545                 550                 555                 560
Val Ile Arg Pro Leu Pro Met Asp Ser Ser Ala Tyr Ser Phe Thr Ala
                565                 570                 575
Phe Val Gly Val Pro Ala Val Glu Phe Ser Phe Met Glu Asp Asp Gln
                580                 585                 590
Ala Tyr Pro Phe Leu His Thr Lys Glu Asp Thr Tyr Glu Asn Leu His
                595                 600                 605
Lys Val Leu Gln Gly Arg Leu Pro Ala Val Ala Gln Ala Val Ala Gln
            610                 615                 620
Leu Ala Gly Gln Leu Leu Ile Arg Leu Ser His Asp Arg Leu Leu Pro
625                 630                 635                 640
Leu Asp Phe Gly Arg Tyr Gly Asp Val Val Leu Arg His Ile Gly Asn
                645                 650                 655
Leu Asn Glu Phe Ser Gly Asp Leu Lys Ala Arg Gly Leu Thr Leu Gln
                660                 665                 670
Trp Val Tyr Ser Ala Arg Gly Asp Tyr Ile Arg Ala Ala Glu Lys Leu
                675                 680                 685
Arg Gln Glu Ile Tyr Ser Ser Glu Glu Arg Asp Glu Arg Leu Thr Arg
            690                 695                 700
Met Tyr Asn Val Arg Ile Met Arg Val Glu Phe Tyr Phe Leu Ser Gln
705                 710                 715                 720
Tyr Val Ser Pro Ala Asp Ser Pro Phe Arg His Ile Phe Met Gly Arg
                725                 730                 735
Gly Asp His Thr Leu Gly Ala Leu Leu Asp His Leu Arg Leu Leu Arg
                740                 745                 750
Ser Asn Ser Ser Gly Thr Pro Gly Ala Thr Ser Ser Thr Gly Phe Gln
                755                 760                 765
Glu Ser Arg Phe Arg Arg Gln Leu Ala Leu Leu Thr Trp Thr Leu Gln
            770                 775                 780
Gly Ala Ala Asn Ala Leu Ser Gly Asp Val Trp Asn Ile Asp Asn Asn
785                 790                 795                 800
Phe

<210> SEQ ID NO 2
<211> LENGTH: 2877
<212> TYPE: DNA
<213> ORGANISM: human genome

<400> SEQUENCE: 2
ctgcaggctt caggagggga cacaagcatg gagcggcttt gggtctatt ccagagagcg      60 caacaactgt ccccaagatc ctctcagacc gtctaccagc gtgtggaagg ccccggaaa    120 gggcacctgg aggaggaaga ggaagacggg gaggaggggg cggagacatt ggcccacttc    180
tgccccatgg agctgagggg ccctgagccc ctgggctcta gacccaggca gccaaacctc    240
attccctggg cggcagcagg acggagggct gcccctacc tggtcctgac ggccctgctg    300
```

-continued

```
atcttcactg gggccttcct actgggctac gtcgccttcc gagggtcctg ccaggcgtgc     360
ggagactctg tgttggtggt cagtgaggat gtcaactatg agcctgacct ggatttccac     420
cagggcagac tctactggag cgacctccag gccatgttcc tgcagttcct ggggagggg     480
cgcctggagg acaccatcag gcaaaccagc cttcgggaac gggtggcagg ctcggccggg     540
atggccgctc tgactcagga cattcgcgcg gcgctctccc gccagaagct ggaccacgtg     600
tggaccgaca cgcactacgt ggggctgcaa ttcccggatc cggctcaccc caacaccctg     660
cactgggtcg atgaggccgg gaaggtcgga gagcagctgc cgctggagga ccctgacgtc     720
tactgccccct acagcgccat cggcaacgtc acgggagagc tggtgtacgc ccactacggg     780
cggcccgaag acctgcagga cctgcgggcc aggggcgtgg atccagtggg ccgcctgctg     840
ctggtgcgcg tggggtgat cagcttcgcc cagaaggtga ccaatgctca ggacttcggg     900
gctcaaggag tgctcatata cccagagcca gcggacttct cccaggaccc acccaagcca     960
agcctgtcca gccagcaggc agtgtatgga catgtgcacc tgggaactgg agaccctac    1020
acacctggct tccccttcctt caatcaaacc cagttccctc cagttgcatc atcaggcctt   1080
cccagcatcc cagcccagcc catcagtgca gacattgcct cccgcctgct gaggaagctc   1140
aaaggccctg tggcccccca agaatggcag gggagcctcc taggctcccc ttatcacctg   1200
ggccccgggc cacgactgcg gctagtggtc aacaatcaca ggacctccac ccccatcaac   1260
aacatcttcg gctgcatcga aggccgctca gagccagatc actacgttgt catcggggcc   1320
cagagggatg catggggccc aggagcagct aaatccgctg tggggacggc tatactcctg   1380
gagctggtgc ggacctttc tccatggtg agcaacggct tccggccccg cagaagtctc    1440
ctcttcatca gctgggacgg tggtgacttt ggaagcgtgg gctccacgga gtggctagaa   1500
ggctacctca gcgtgctgca cctcaaagcc gtagtgtacg tgagcctgga caacgcagtg   1560
ctggggatg acaagtttca tgccaagacc agccccttc tgacaagtct cattgagagt    1620
gtcctgaagc aggtggattc tcccaaccac agtgggcaga ctctctatga acaggtggtg   1680
ttcaccaatc ccagctggga tgctgaggtg atccggcccc tacccatgga cagcagtgcc   1740
tattccttca cggcctttgt gggagtccct gccgtcgagt tctcctttat ggaggacgac   1800
caggcctacc cattcctgca cacaaaggag gacacttatg agaacctgca taaggtgctg   1860
caaggccgcc tgcccgccgt ggcccaggcc gtggcccagc tcgcagggca gctcctcatc   1920
cggctcagcc acgatcgcct gctgccctc gacttcggcc gctacgggga cgtcgtcctc   1980
aggcacatcg ggaacctcaa cgagttctct ggggacctca aggcccgcgg gctgaccctg   2040
cagtgggtgt actcggcgcg gggggactac atccgggcgg cggaaaagct gcggcaggag   2100
atctacagct cggaggagag agacgagcga ctgacacgca tgtacaacgt gcgcataatg   2160
cgggtggagt tctacttcct ttcccagtac gtgtcgccag ccgactcccc gttccgccac   2220
atcttcatgg gccgtggaga ccacacgctg gcgccctgc tggaccacct gcggctgctg   2280
cgctccaaca gctccgggac ccccggggcc acctcctcca ctggcttcca ggagagccgt   2340
ttccggcgtc agctagccct gctcacctgg acgctgcaag gggcagccaa tgcgcttagc   2400
ggggatgtct ggaacattga taacaacttc tgaggccctg gggatcctca catcccgtc    2460
ccccagtcaa gagctcctct gctcctcgct tgaatgattc agggtcaggg aggtggctca   2520
gagtccacct ctcattgctg atcaatttct cattaccct acacatctct ccacggagcc    2580
cagaccccag cacagatatc cacacacccc agccctgcag tgtagctgac cctaatgtga   2640
cggtcatact gtcggttaat cagagagtag catcccttca atcacagccc cttccccttt   2700
```

-continued

| | |
|---|---:|
| ctggggtcct ccatacccta g agaccactct gggaggtttg ctaagccctg ggacctggcc | 2760 |
| agctctgtta gtgggagaga tcgctggcac catagcctta tggccaacag gtggtctgtg | 2820 |
| gtgaaagggg cgtggagttt caatatcaat aaaccacctg atatcaataa gccaaaa | 2877 |

<210> SEQ ID NO 3
<211> LENGTH: 2519
<212> TYPE: DNA
<213> ORGANISM: human genome

<400> SEQUENCE: 3

| | |
|---|---:|
| gcgtccgcgg ggagcgctct tttcctaaac tcaggaaccc ctcgccgccc ctgcccctgg | 60 |
| cgaccccacg tctctggcat ccttccctct tccctccctc tcctccgggc gcccaaaaaa | 120 |
| gtccccacct ctccccgctt aggcaaacca gccttcggga acgggtggca ggctcggccg | 180 |
| ggatggccgc tctgactcag gacattcgcg cggcgctctc ccgccagaag ctggaccacg | 240 |
| tgtggaccga cacgcactac gtggggctgc aattcccgga tccggctcac cccaacaccc | 300 |
| tgcactgggt cgatgaggcc gggaaggtcg agagcagct gccgctggag gaccctgacg | 360 |
| tctactgccc ctacagcgcc atcggcaacg tcacgggaga gctggtgtac gcccactacg | 420 |
| gcggcccga agacctgcag gacctgcggg ccaggggcgt ggatccagtg gccgcctgc | 480 |
| tgctggtgcg cgtggggtg atcagcttcg cccagaaggt gaccaatgct caggacttcg | 540 |
| ggctcaagg agtgctcata tacccagagc cagcggactt ctcccaggac ccacccaagc | 600 |
| caagcctgtc cagccagcag gcagtgtatg gacatgtgca cctgggaact ggagacccct | 660 |
| acacacctgg cttcccttcc ttcaatcaaa cccagttccc tccagttgca tcatcaggcc | 720 |
| ttcccagcat cccagcccag cccatcagtg cagacattgc ctcccgcctg ctgaggaagc | 780 |
| tcaaaggccc tgtggccccc aagaatggc aggggagcct cctaggctcc ccttatcacc | 840 |
| tgggccccgg gccacgactg cggctagtgg tcaacaatca caggacctcc accccccatca | 900 |
| acaacatctt cggctgcatc gaaggccgct cagagccaga tcactacgtt gtcatcgggg | 960 |
| cccagaggga tgcatgggcc ccaggagcag ctaaatccgc tgtggggacg gctatactcc | 1020 |
| tggagctggt gcggacctttt tcctccatgg tgagcaacgg cttccggccc cgcagaagtc | 1080 |
| tcctcttcat cagctgggac ggtggtgact ttggaagcgt gggctccacg gagtggctag | 1140 |
| aaggctacct cagcgtgctg cacctcaaag ccgtagtgta cgtgagcctg gacaacgcag | 1200 |
| tgctggggga tgacaagttt catgccaaga ccagccccct tctgacaagt ctcattgaga | 1260 |
| gtgtcctgaa gcaggtggat tctcccaacc acagtgggca gactctctat gaacaggtgg | 1320 |
| tgttcaccaa tcccagctgg gatgctgagg tgatccggcc cctacccatg acagcagtg | 1380 |
| cctattcctt cacggccttt gtgggagtcc ctgccgtcga gttctccttt atggaggacg | 1440 |
| accaggccta cccattcctg cacacaaagg aggacactta tgagaacctg cataaggtgc | 1500 |
| tgcaaggccg cctgcccgcc gtgggcccag cgtggccca gctcgcaggg cagctcctca | 1560 |
| tccggctcag ccacgatcgc ctgctgcccc tcgacttcgg ccgctacggg acgtcgtcc | 1620 |
| tcaggcacat cggaacctc aacgagttct ctggggacct caaggcccgc gggctgaccc | 1680 |
| tgcagtgggt gtactcggcg cgggggact acatccgggc ggcggaaaag ctgcggcagg | 1740 |
| agatctacag ctcggaggag agagacgagc gactgacacg catgtacaac gtgcgcataa | 1800 |
| tgcgggtgga gttctacttc ctttcccagt acgtgtcgcc agccgactcc ccgttccgcc | 1860 |
| acatcttcat gggccgtgga gaccacacg tgggcgccct gctggaccac ctgcggctgc | 1920 |
| tgcgctccaa cagctccggg accccgggg ccacctcctc cactggcttc caggagagcc | 1980 |

```
gtttccggcg tcagctagcc ctgctcacct ggacgctgca aggggcagcc aatgcgctta   2040
gcggggatgt ctggaacatt gataacaact tctgaggccc tggggatcct cacatccccg   2100
tcccccagtc aagagctcct ctgctcctcg cttgaatgat tcagggtcag ggaggtggct   2160
cagagtccac ctctcattgc tgatcaattt ctcattaccc ctacacatct ctccacggag   2220
cccagacccc agcacagata tccacacacc ccagccctgc agtgtagctg accctaatgt   2280
gacggtcata ctgtcggtta atcagagagt agcatccctt caatcacagc cccttcccct   2340
ttctggggtc ctccatacct agagaccact ctgggaggtt tgctaggccc tgggacctgg   2400
ccagctctgt tagtgggaga gatcgctggc accatagcct tatggccaac aggtggtctg   2460
tggtgaaagg ggcgtggagt ttcaatatca ataaaccacc tgatatcaat aagccaaaa    2519
```